United States Patent
Sano et al.

(10) Patent No.: US 11,268,916 B2
(45) Date of Patent: Mar. 8, 2022

(54) X-RAY PHASE IMAGING SYSTEM

(71) Applicant: Shimadzu Corporation, Kyoto (JP)

(72) Inventors: Satoshi Sano, Kyoto (JP); Koichi Tanabe, Kyoto (JP); Yukihisa Wada, Kyoto (JP); Satoshi Tokuda, Kyoto (JP); Akira Horiba, Kyoto (JP); Naoki Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 17/287,412

(22) PCT Filed: Jul. 22, 2019

(86) PCT No.: PCT/JP2019/028662
§ 371 (c)(1),
(2) Date: Apr. 21, 2021

(87) PCT Pub. No.: WO2020/095482
PCT Pub. Date: May 14, 2020

(65) Prior Publication Data
US 2021/0364453 A1 Nov. 25, 2021

(30) Foreign Application Priority Data
Nov. 6, 2018 (JP) .............................. JP2018-208933

(51) Int. Cl.
*G01N 23/041* (2018.01)
*A61B 6/02* (2006.01)
*G01N 23/046* (2018.01)
*A61B 6/00* (2006.01)

(52) U.S. Cl.
CPC ........... *G01N 23/041* (2018.02); *A61B 6/025* (2013.01); *G01N 23/046* (2013.01); *A61B 6/484* (2013.01); *G01N 2223/401* (2013.01)

(58) Field of Classification Search
None
See application file for complete search history.

(56) References Cited

U.S. PATENT DOCUMENTS

| | | | |
|---|---|---|---|
| 2007/0183579 A1* | 8/2007 | Baumann | A61B 6/4291 378/145 |
| 2010/0074395 A1* | 3/2010 | Popescu | A61B 6/06 378/16 |
| 2018/0356355 A1 | 12/2018 | Momose et al. | |

FOREIGN PATENT DOCUMENTS

| | | |
|---|---|---|
| JP | 2017-044603 A | 3/2017 |
| JP | 2017-072399 A | 4/2017 |

OTHER PUBLICATIONS

Written Opinion by the International Search Authority for PCT application No. PCT/JP2019/028662 dated Sep. 24, 2019, submitted with a machine translation.

* cited by examiner

*Primary Examiner* — David P Porta
*Assistant Examiner* — Mamadou Faye
(74) *Attorney, Agent, or Firm* — Muir Patent Law, PLLC

(57) ABSTRACT

This X-ray phase imaging system (100) includes an X-ray source (1), a detector (2), a first grating group (3), a second grating group (4), a moving mechanism (5), and an image processing unit (6). The moving mechanism is configured to relatively move a subject (T) and the imaging system (9) such that the subject (T) passes through a first grating region (R1) and a second grating region (R2). The image processing unit is configured to generate a first phase-contrast image (14a) and a second phase-contrast image (14b).

15 Claims, 19 Drawing Sheets

First Embodiment

FIG. 4
First Embodiment
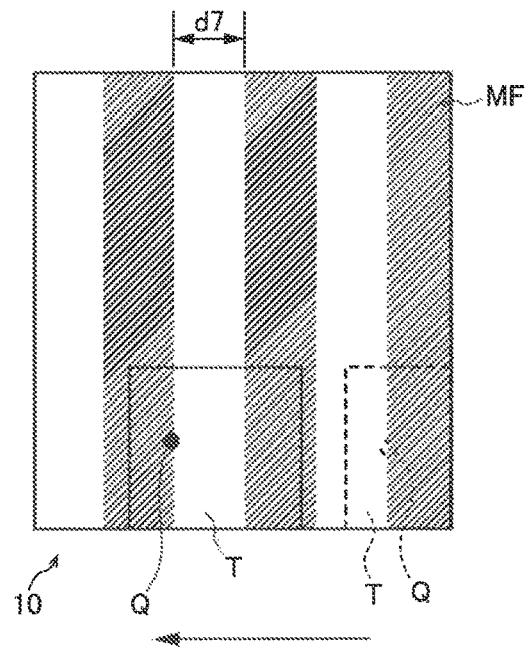
FIG. 5
First Embodiment
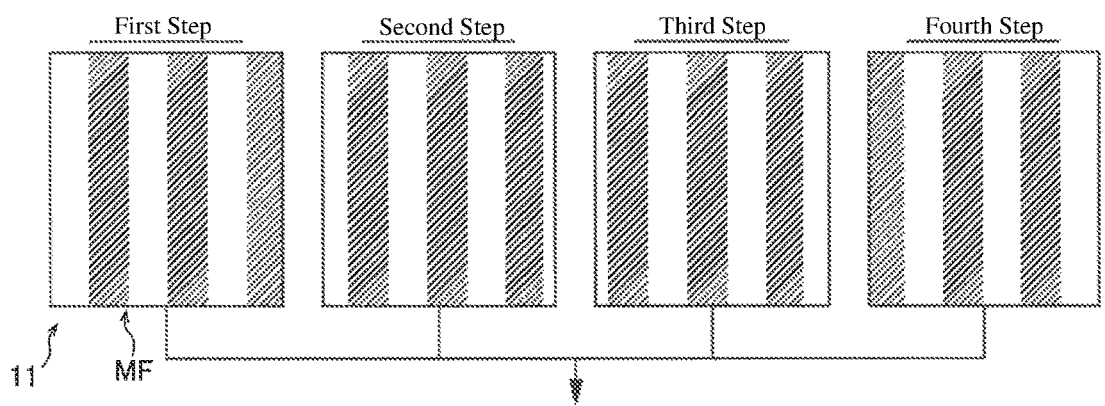
Phase information of Moire fringe
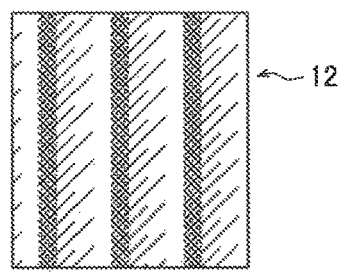

First Embodiment

First Embodiment

First Embodiment

First Embodiment

First Embodiment

First Embodiment

First Embodiment

Comparative Example

First Embodiment

First Embodiment

First composite image generation processing

Second Embodiment

Third Embodiment

Third Embodiment

Third Embodiment

Third Embodiment

Fourth Embodiment

Fourth Embodiment

First Modification

Second Modification

X-RAY PHASE IMAGING SYSTEM

TECHNICAL FIELD

The present invention relates to an X-ray phase imaging system and in particular, to an X-ray phase imaging system for performing imaging while relatively moving a subject and an imaging system.

BACKGROUND ART

Conventionally, an X-ray phase imaging system for performing imaging while relatively moving a subject and an imaging system is known. Such an X-ray phase imaging system is disclosed, for example, in Japanese Unexamined Patent Application Publication No. 2017-44603.

The X-ray phase imaging system disclosed in Japanese Unexamined Patent Application Publication No. 2017-44603 is provided with an X-ray source, a grating group including a first grating, a second grating, and a third grating, a detection unit, a transfer unit for moving the subject, a pixel arithmetic unit, and an image operation unit. The X-ray phase imaging system disclosed in Japanese Unexamined Patent Application Publication No. 2017-44603 is configured to generate a phase-contrast image including an absorption image, a phase differential image, and a dark-field image by capturing a plurality of images while moving a subject in a period direction of a Moire fringe caused by a plurality of gratings irradiated with X-rays. Note that an absorption image is an image generated based on the attenuation of X-rays caused when the X-rays have passed through a subject. Also note that a phase differential image is an image generated based on a phase deviation of X-rays caused when the X-rays have passed through a subject. Further, a dark-field image is a visibility image acquired by the change of the visibility based on small-angle scattering (refraction) of X-rays by a subject. The dark-field image is also called a small-angle scattering image. The "visibility" refers to sharpness.

Here, a phase differential image and a dark-field image are images acquired by imaging a subject based on the phase shift of X-rays by a subject and the refraction of X-rays in a direction perpendicular to the direction of the grating (the direction in which the grating extends). That is, it is sensitive in a direction perpendicular to the extending direction of the grating but not sensitive in a direction along the extending direction of the grating. Thus, depending on the orientation of the grating with respect to the subject, there are areas that are not imaged on a phase differential image and a dark-field image. Therefore, when generating a phase differential image and a dark-field image, it is preferable to perform imaging by changing the orientation of the grating with respect to the subject.

PRIOR ART DOCUMENT

Patent Document

Patent Document 1: Japanese Unexamined Patent Application Publication No. 2017-44603

SUMMARY OF THE INVENTION

Problems to be Solved by the Invention

However, according to the configuration of Japanese Unexamined Patent Application Publication No. 2017-44603, a subject is imaged while moving the subject with respect to the grating arranged in a predetermined direction. Therefore, in the configuration of Japanese Unexamined Patent Application Publication No. 2017-44603, in order to perform imaging by changing the orientation of the grating with respect to the subject, after performing imaging once in a predetermined orientation, imaging is performed again while moving the subject with the orientation of the subject or the grating changed.

The present invention has been made to solve the above-described problems, and an object of the present invention is to provide an X-ray phase imaging system capable of imaging a subject by changing an orientation of a grating with respect to the subject without performing imaging while moving the subject again with the orientation of the subject or the grating changed.

Means for Solving the Problem

In order to attain the above-described object, an X-ray phase imaging system according to one aspect of the present invention, includes:

an X-ray source;

a detector configured to detect X-rays emitted from the X-ray source;

a first grating group including a plurality of gratings arranged along an optical axis direction of the X-rays between the X-ray source and the detector, an extending direction of each of the plurality of gratings being along a first direction;

a second grating group including a plurality of gratings arranged along the optical axis direction of the X-rays between the X-ray source and the detector, the second grating group being arranged side by side with the first grating group in a direction intersecting with the optical axis direction, an extending direction of each of the plurality of gratings of the second grating group being along a second direction different from the first direction;

a moving mechanism configured to relatively move a subject and an imaging system, the imaging system being composed of the X-ray source, the detector, the first grating group, and the second grating group; and an image processing unit configured to generate a phase-contrast image based on a signal detected by the detector, wherein the moving mechanism is configured to relatively move the subject and the imaging system such that the subject passes through a first grating region in which the first grating group is arranged and a second grating region in which the second grating group is arranged, and wherein the image processing unit is configured to generate a first phase-contrast image when the subject has passed through the first grating region and a second phase-contrast image when the subject has passed through the second grating region.

In the X-ray phase imaging system according to one aspect of the present invention, as described above, it is provided with a moving mechanism that relatively moves a subject and a grating such that the subject passes through the first grating region in which the first grating group is arranged and the second grating region in which the second grating group is arranged. With this, by imaging the subject by passing through the first grating region and the second grating region, the subject can be imaged by the first grating group and the second grating group different in the extending direction of the grating. As a result, imaging can be performed with the orientation of the grating changed with respect to the subject without performing imaging while moving the subject again with the orientation of the subject or the grating changed. Thus, it is possible to simplify the imaging operation, and it is also possible to shorten the imaging time.

In the X-ray phase imaging system according to the first aspect of the present invention, preferably, the first grating group and the second grating group are arranged such that the first direction and the second direction are substantially perpendicular to each other. With this configuration, since the first direction and the second direction are substantially perpendicular to each other, regardless of the arrangement orientation of the subject, in either the first grating group or the second grating group, it is possible to extract the X-ray phase shift or the X-ray refraction by the subject. Consequently, the subject can be imaged in either the first phase-contrast image or the second phase-contrast image, regardless of the arrangement direction of the subject.

In the X-ray phase imaging system according to the first aspect of the present invention, preferably, the image processing unit is configured to generate a first composite image in which the first phase-contrast image and the second phase-contrast image are composed. With this configuration, it is possible to collectively grasp the sensitivity in the first direction and the second direction in the first composite image in which the second phase-contrast image having sensitivity in the first direction and the first phase-contrast image having sensitivity in the second direction are composed. Consequently, the internal structure of the subject can be grasped in detail.

In the X-ray phase imaging system according to the first aspect of the present invention, preferably, the X-rays that have passed through the first grating group and the X-rays that have passed through the second grating group are each detected by a common detector. With this configuration, by providing a single detector, it is possible to detect the X-rays that have passed through the first grating group and the X-rays that have passed through the second grating group. Consequently, as compared with the case in which a detector for detecting the X-rays passing through the first grating group and a detector for detecting the X-rays passing through the second grating group are provided, it is possible to suppress the increase in the number of components.

In the X-ray phase imaging system according to the first aspect of the present invention, preferably, the first grating group and the second grating group are each arranged within an irradiation range of the X-rays emitted from a common X-ray source. With this configuration, the X-rays can be emitted to the first grating group and the second grating group by providing one X-ray source. As a result, it is possible to suppress the increase in the number of components as compared with the case in which an X-ray source for irradiating the first grating group with X-rays and an X-ray source for irradiating the second grating group with X-rays are separately provided.

In the X-ray phase imaging system according to the first aspect of the present invention, preferably, the first grating group and the second grating group each include a first grating for enhancing coherence of the X-rays emitted from the X-ray source, a second grating for forming a self-image, and a third grating for interfering with the self-image of the second grating, and the first grating of the first grating group and the first grating of the second grating group are formed integrally, the second grating of the first grating group and the second grating of the second grating group are formed separately, and the third grating of the first grating group and the third grating of the second grating group are formed separately.

With this configuration, by integrally forming the first grating of the first grating group and the first grating of the second grating group, which are arranged in the vicinity of the X-ray source, it is possible to make the distance from the X-ray source to the first grating of the first grating group and the distance from the X-ray source to the first grating of the second grating group substantially equal. Further, for example, in a case where imaging is performed with a Moire fringe formed in advance, it is required to make the directions of the periods of the Moire fringes substantially equal between the Moire fringe by the first grating group and the Moire fringe by the second grating group. However, since the first grating group and the second grating group are arranged such that the directions in which gratings extend are different from each other, the relative position of each grating for forming a Moire fringe is different between the first grating group and the second grating group. Thus, each grating of the first grating group and each grating of the second grating of the second grating group can be arranged at a relative position suitable for forming a Moire fringe respectively by forming the second grating of the first grating group and the second grating of the second grating group separately and by forming the third grating of the first grating group and the third grating of the second grating group separately.

Further, for example, in order to acquire the phase information of a Moire fringe formed in advance, in a case where imaging is performed while translating the second grating or the third grating in each of the first grating group and the second grating group, since the extending directions of the gratings are arranged differently in the first grating group and the second grating group. Therefore, the direction for translating the gratings differs between the first grating group and the second grating group. By forming the first grating of the second grating group and the second grating of the second grating group with separate members and by forming the third grating of the first grating group and the third grating of the second grating group with separate members, it becomes possible to provide a moving mechanism on each of the gratings to be translated among the gratings of the first grating group and the second grating group. Thus, imaging can be performed while translating the gratings to be translated in directions different from each other in the first grating group and the second grating group.

In the X-ray phase imaging system according to the first aspect of the present invention, preferably, the image processing unit is configured such that based on a plurality of images captured while relatively moving the subject and the imaging system in each of the first grating region and the second grating region and phase information of Moire fringes generated in the plurality of images, a pixel value in each pixel of the subject in the plurality of images and a phase value of the Moire fringe generated in each pixel are associated, and based on position information of a pixel of the subject at the same position in the plurality of images and a pixel value of each pixel value associated with the phase value, the first phase-contrast image and the second phase-contrast image are generated by aligning pixels of the subject at the same position in the plurality of images in each of the first grating region and the second grating region.

With this configuration, it is possible to generate a first phase-contrast image and a second phase-contrast image with the pixel value of a pixel of the subject at the same position in each image and each phase value corresponding to the pixel of the subject at the same position in each image.

Thus, for example, as compared with the case in which a first phase-contrast image and a second phase-contrast image are generated using the mean value of pixel values included in each region acquired by dividing the region of one period of the Moire fringe, it is possible to generate the first phase-contrast image and the second phase-contrast image by using the pixel value of each pixel imaged the same position. Consequently, it is possible to suppress the degradation of the image quality of the first phase-contrast image and the second phase-contrast image due to an error in the pixel value used for generating the first phase-contrast image and the second phase-contrast image.

In the X-ray phase imaging system according to the first aspect of the present invention, preferably, the moving mechanism is configured to continuously move the subject when imaging the subject, and the image processing unit is configured to generate the first phase-contrast image and the second phase-contrast image based on the acquired continuous images. With this configuration, when generating a continuous first phase-contrast image and second phase-contrast image, for example, unlike a conventional fringe scanning method of generating a continuous first phase-contrast image and second phase-contrast image by repeating the movement and the imaging of the subject, by performing imaging while continuously moving the subject, it is possible to generate a continuous first phase-contrast image and second phase-contrast image. As a result, the image capturing time can be shortened as compared with a conventional fringe scanning method.

In the configuration of generating a first phase-contrast image and a second phase-contrast image by associating a pixel value in each pixel of the subject and a phase value of a Moire fringe in each pixel, preferably, the moving mechanism is configured to move the subject by a predetermined distance at a time when imaging the subject, and the image processing unit is configured to generate the first phase-contrast image and the second phase-contrast image based on the image acquired while moving the subject by the predetermined distance at a time. With this configuration, as compared with the case of performing imaging while continuously moving a subject, it is possible to reduce the number of images when generating a first phase-contrast image and a second phase-contrast image. As a result, the imaging time can be further shortened. In addition, for example, in a case where it is used in medical applications, it is possible to suppress an increase in the amount of exposure.

In the configuration of generating a first phase-contrast image and a second phase-contrast image by associating a pixel value at each pixel of the subject and a phase value of a Moire fringe at each pixel, preferably, the image processing unit is configured to generate position calibration data used for aligning respective pixels of the subject at the same position in the plurality of images based on a plurality of position calibration images captured while relatively moving the marker and the imaging system. With this configuration, by using the position calibration data, it becomes possible to acquire the position in each image of the pixel of the subject at the same position, and therefore it is possible to calculate the movement amount of the subject. As a result, for example, even in a case where the movement amount of the subject and the movement amount of the marker are not the same, the movement amount of the subject can be acquired, so that the alignment of the pixel of the subject at the same position in a plurality of images can be performed.

In the configuration of generating position calibration data based on a plurality of position calibration images captured while relatively moving the marker and the imaging system, preferably, the position calibration data is generated based on a command value related to a movement amount input to the moving mechanism when relatively moving the marker and the imaging system by the moving mechanism and a movement amount of the marker or the imaging system in the position calibration image when the marker and the imaging system are relatively moved based on the command value. With this configuration, even in a case where there occurred an error between the command value related to the movement amount input to the moving mechanism and the movement amount of the marker or the imaging system, an accurate movement amount can be acquired by the position calibration data. As a result, it becomes possible to accurately align each pixel of the subject at the same position in a plurality of images, so that it is possible to further suppress deterioration of the image quality of the resulting phase-contrast image.

In the case, preferably, the position calibration data is generated by acquiring an approximate expression showing a relation between the command value and the movement amount of the marker or the imaging system, based on a position of each pixel of the marker at the same position in the plurality of position calibration images. With this configuration, by acquiring the approximate expression based on the position of each pixel of the marker at the same position in the plurality of position calibration images, the relation between the command value related to the movement amount to a position different from the position where the plurality of position calibration images are captured and the movement amount of the marker or the imaging system can be calculated using the approximate expression. Consequently, for example, when imaging a subject, even in a case where the subject is moved to the position different from the position to which the marker or the imaging system has been moved, the movement amount of the subject can be acquired.

In the X-ray phase imaging system according to the first aspect of the present invention, preferably, the image processing unit is configured to generate a phase image, based on a phase differential image when the subject has passed through the first grating region and a phase differential image when the subject has passed through the second grating region. With this configuration, as compared with the configuration of generating a phase image by integrating in a predetermined direction, in either one of the phase differential image when the subject has passed through the first grating region or a phase differential image when the subject has passed through the second grating region, it is possible to suppress the occurrence of artifacts in the phase image in the integration direction. As a result, it is possible to suppress degradation of the image quality of the phase image.

In the X-ray phase imaging system according to the first aspect of the present invention, preferably, it further includes a position information acquisition unit configured to acquire a tomographic position of a tomographic plane which is an imaging target, in the optical axis direction and the image processing unit is configured to generate the first phase-contrast image and the second phase-contrast image in the tomographic plane, by acquiring a phase distribution in the tomographic plane, based a plurality of images in which the subject was imaged at a plurality of relative positions of the imaging system and the subject in a predetermined direction and the acquired tomographic position. With this configuration, the position (tomographic position) of tomographic plane in the optical axis direction in which an internal structure to be imaged exists can be acquired by the position information acquisition unit. Since the incidence angle of the X-rays with respect to the point on the tomographic plane is determined by the relative position between the imaging system and the subject, the position of the point on the tomographic plane in each X-ray image can be identified by the information of the tomographic position and the relative position when the X-ray image is captured. This allows the image processing unit to acquire the phase distribution in a particular tomographic plane indicated by the tomographic position based on the acquired tomographic position information and the respective X-ray images at the plurality of relative positions. Consequently, from the phase distribution in the tomographic plane at the tomographic position acquired by the position information acquisition unit, a phase-contrast image (tomographic image) in which blurring of an image is suppressed for the internal structure contained in the tomographic plane can be acquired. As a result, even in the case of a subject having a large thickness, it is possible to suppress the deterioration in the visibility of the internal structure.

In the X-ray phase imaging system according to the first aspect of the present invention, preferably, the moving mechanism is configured to relatively move the subject and the imaging system such that the subject passes through no grating region where the first grating group and the second grating group are not arranged, and the image processing unit is configured to display the first phase-contrast image and the second phase-contrast image, and an absorption image acquired when the subject has passed through the no grating region by arranging them side by side, or display a second composite image in which the first phase-contrast image and the second phase-contrast image, and the absorption image are composed. With this configuration, without performing imaging with the first grating group retracted or without performing imaging using another imaging apparatus not provided with a grating, it is possible to generate a first phase-contrast image and a second phase-contrast image using an absorption image captured without interposing a grating and a grating. The X-rays that have reached the no grating region reach the detector without passing through a grating, it is possible to suppress the attenuation of X-rays due to a grating, in particular, the attenuation of X-rays due to a low-energy side. Consequently, as compared with an absorption image generated by X-rays arriving through the first grating region and the second grating region, the contrast of the absorption image generated by X-rays arriving through the no grating region can be improved.

Effects of the Invention

According to the present invention, as described above, it is possible to provide an X-ray phase imaging system capable of performing imaging by changing the orientation of a grating with respect to a subject without performing imaging while moving the subject again with the orientation of the subject or the grating changed.

BRIEF DESCRIPTION OF THE DRAWINGS

FIG. 4 is a schematic diagram of an image captured while continuously moving the subject by the X-ray phase imaging system according to the first embodiment.

FIG. 5 is a schematic diagram for explaining a configuration in which the phase information of a Moire fringe acquired by the X-ray phase imaging system according to the first embodiment is acquired.

EMBODIMENTS FOR CARRYING OUT THE INVENTION

Hereinafter, some embodiments in which the present invention is embodied will be described with reference to the attached drawings.

First Embodiment

Referring to FIG. 1 to FIG. 15, the configuration of the X-ray phase imaging system 100 according to a first embodiment of the present invention and a method of generating a first phase-contrast image 14a (see FIG. 13), a second phase-contrast image 14b (see FIG. 13), and a first composite image 19 (see FIG. 15) by the X-ray phase imaging system 100 will be described.
(Configuration of X-Ray Phase Imaging System)

First, referring to FIG. 1, the configuration of the X-ray phase imaging system 100 according to the first embodiment will be described.

Figure 1:
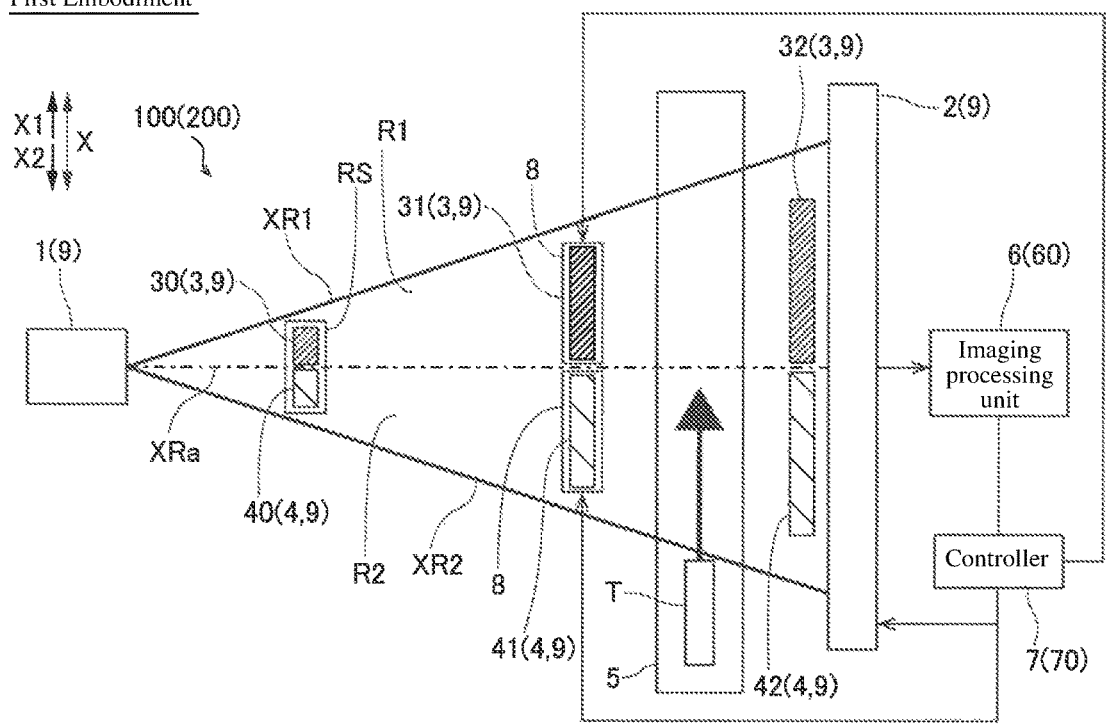
FIG. 1 is a schematic diagram showing the entire configuration of an X-ray phase imaging system according to a first embodiment.

As shown in FIG. 1, the X-ray phase imaging system 100 is a system that utilizes a Talbot effect to image the interior of a subject T. The X-ray phase imaging system 100 can be used, for example, in a non-destructive inspection application to image the inside of a subject T as an object.

FIG. 1 is a view of the X-ray phase imaging system 100 as viewed from the Y-direction. As shown in FIG. 1, the X-ray phase imaging system 100 is provided with an X-ray source 1, a detector 2, a first grating group 3, a second grating group 4, a moving mechanism 5, an image processing unit 6, a controller 7, and a grating moving mechanism 8. Note that, in this specification, the direction from the X-ray source 1 toward the first grating 30 is defined as a Z2-direction, the opposite direction thereof is defined as a Z1-direction. In the example shown in FIG. 1, the direction along the horizontal direction is defined as a Z-direction. Further, the left-right direction in the plane perpendicular to the Z-direction is defined as an X-direction, the left direction (the upward direction of the paper surface in FIG. 1) is defined as an X1-direction, and the right direction (the downward direction of the paper surface in FIG. 1) is defined as an X2-direction. Further, the up-down direction in the plane perpendicular to the Z-direction is defined as a Y-direction, the upward direction (the direction toward the back of the paper surface in FIG. 1) is defined as a Y2-direction, and the downward direction (the direction toward the front side of the paper surface in FIG. 1) is defined as a Y1-direction.

The X-ray source 1 generates X-rays when a high voltage is applied. The X-ray source 1 is configured to emit the generated X-rays toward the direction (Z2-direction) along the optical axis XRa. Note that in the example shown in FIG. 1, the X-ray source 1 emits X-rays to the region surrounded by the straight line XR1 and the straight line XR2.

The detector 2 is configured to detect X-rays, convert the detected X-rays into an electric signal, and read the converted electric signal as an image signal. The detector 2 is, for example, an FPD (Flat Panel Detector). The detector 2 is composed of a plurality of conversion elements (not shown) and pixel electrodes (not shown) arranged on the plurality of conversion elements. The plurality of conversion elements and the plurality of pixel electrodes are arranged in an array in the X-direction and the Y-direction at a predetermined period (pixel pitch). The detector 2 is configured to output the acquired image signal to the image processing unit 6.

The first grating group 3 includes a plurality of gratings arranged along the optical axis XRa direction of X-rays (Z-direction) between the X-ray source 1 and the detector 2 with the extending direction of the grating being along the first direction (Y-direction). Specifically, the first grating group 3 includes a first grating 30, a second grating 31, and a third grating 32. Note that the Y-direction is one example of the "first direction" recited in claims. Further note that the Z-direction is one example of the "optical axis direction" recited in claims.

The second grating group 4 is arranged side by side with the first grating group 3 in a direction (X-direction) intersecting with the Z-direction between the X-ray source 1 and the detector 2, and includes a plurality of gratings arranged along the Z-direction with the extending direction of the grating being along the second direction (X-direction) different from the Y-direction. Specifically, the second grating group 4 includes a first grating 40, a second grating 41, and a third grating 42. Note that the X-direction is one example of the "direction intersecting with the optical axis direction" and the "second direction" recited in claims.

The first grating 30 is arranged between the X-ray source 1 and the second grating 31 and is irradiated with X-rays from the X-ray source 1. The first grating 30 is provided to enhance the coherence of the X-rays emitted from the X-ray source 1 by a Lau effect. The first grating 30 is configured so that the X-rays that have passed through the X-ray transmission portion 30a serve as a line light source. When the pitch of the three gratings (the first grating 30, the second grating 31, and the third grating 32) and the distance between the gratings satisfy certain conditions, it is possible to enhance the coherence of the X-rays emitted from the X-ray source 1. This is called a Lau effect.

The second grating 31 is provided to form a self-image of the second grating 31 by a Talbot effect. When coherent X-rays pass through a grating in which slits are formed, an image (self-image) of the grating is formed at a position away from the grating by a predetermined distance (Talbot distance). This is called a Talbot effect.

The third grating 32 is arranged between the second grating 31 and the detector 2 and is irradiated with X-rays that have passed through the second grating 31. The third grating 32 is arranged at a position away from the second grating 31 by a predetermined Talbot distance. The third grating 32 interferes with the self-image of the second grating 31 to form a Moire fringe MF (see FIG. 4).

The first grating 40, the second grating 41, and the third grating 42 are arranged for similar purposes as the first grating 30, the second grating 31, and the third grating 32, respectively.

The moving mechanism 5 is configured to move a subject T or an imaging system 9 in the X-direction under the control of a controller 7. The imaging system 9 is composed of the X-ray source 1, the detector 2, the first grating group 3, and the second grating group 4. In the example shown in FIG. 1, the moving mechanism 5 is configured to relatively move the subject T and the imaging system 9 by moving the subject T from the X2-direction to the X1-direction. Specifically, the moving mechanism 5 is configured to relatively move the subject T and the imaging system 9 such that the subject T passes through the first grating region R1 in which the first grating group 3 is arranged and the second grating region R2 in which the second grating group 4 is arranged. The moving mechanism 5 is configured, for example, by a belt conveyor or various kinds of linear motion mechanisms. Note that in the first embodiment, between the X-ray source 1 and the detector 2, the region surrounded by the straight line XR1 and the optical axis XRa of the X-rays is defined as the first grating region R1. Further, between the X-ray source 1 and the detector 2, the region surrounded by the straight line XR2 and the optical axis XRa of the X-rays is defined as the second grating region R2.

The image processing unit 6 is configured to generate a phase-contrast image 14 (see FIG. 12) based on the image signal output from the detector 2. The image processing unit 6 is configured to generate a first phase-contrast image 14a when the subject T has passed through the first grating region R1 and a second phase-contrast image 14b when the subject T has passed through the second grating region R2. Further, the image processing unit 6 is configured to generate a first composite image 19 in which a first phase-contrast image 14a and a second phase-contrast image 14b are composed. The image processing unit 6 includes, for example, a processor, such as, e.g., a GPU (Graphics Processing Unit) and an FPGA (Field-Programmable Gate Array) configured for image processing. The detailed configuration for generating the first phase-contrast image 14a, the second phase-contrast image 14b, and the first composite image 19 by the image processing unit 6 will be described later.

The controller 7 is configured to control the moving mechanism 5 to move the subject T in the X-direction. The controller 7 is configured to control the grating moving mechanism 8 to move the second grating 31 and the second grating 41. Further, the controller 7 is configured to generate a Moire fringe MF (see FIG. 4) on the detection surface of the detector 2 by adjusting the position of the second grating 31 and the second grating 41 by controlling the grating moving mechanism 8. The controller 7 includes, for example, a CPU (Central Processing Unit), a ROM (Read Only Memory), and a RAM (Random Access Memory).

The grating moving mechanism 8 is configured to move the second grating 31 and the second grating 41 under the control of the controller 7. Further, the grating moving mechanism 8 is configured to produce a Moire fringe MF (see FIG. 4) by adjusting the position of the second grating 31 and the second grating 41 under the control of the controller 7. The detailed configuration in which the grating moving mechanism 8 moves the grating will be described later. Further, in the example shown in FIG. 1, two grating moving mechanisms 8 respectively holds the second grating 31 and the second grating 41.

(Structure of Each Grating)

Next, referring to FIG. 2, the structure of the first grating 30, the second grating 31, and the third grating 32 included in the first grating group 3, and the structure of the first grating 40, the second grating 41, and the third grating 42 included in the second grating group 4 will be described.

(First Grating Group)

Figure 2:
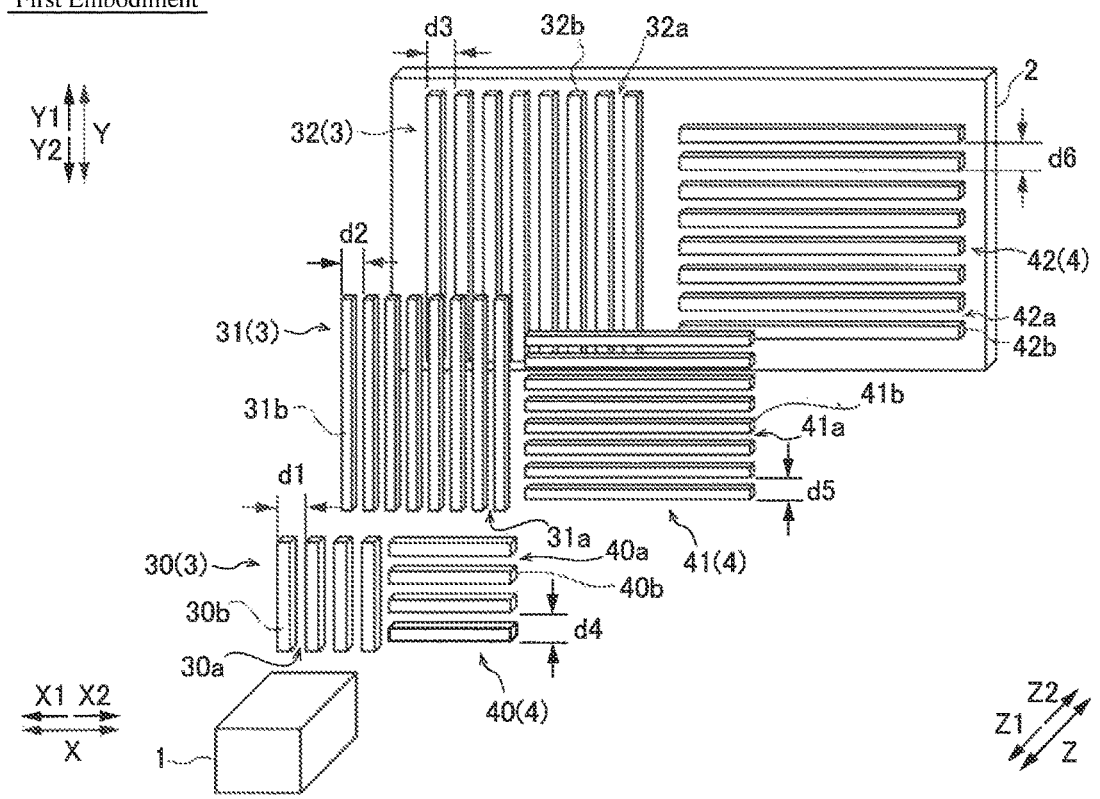
FIG. 2 is a schematic diagram for explaining the construction and the arrangement of a first grating group and the construction and the arrangement of a second grating group.

As shown in FIG. 2, the first grating 30 has a plurality of X-ray transmission portions 30a and a plurality of X-ray absorption portions 30b which are arranged at a predetermined period (pitch) d1 in the X-direction. The X-ray transmission portion 30a and the X-ray absorption portion 30b are each formed so as to extend linearly. Further, the X-ray transmission portion 30a and the X-ray absorption portion 30b are each formed so as to extend in parallel with each other. Further, the first grating 30 is configured to make the X-rays that have passed through the respective X-ray transmission portions 30a as a line light source corresponding to the position of each X-ray transmission portion 30a.

The second grating 31 has a plurality of slits 31a and a plurality of X-ray phase change portions 31b. Each slit 31a and each X-ray phase change portion 31b are arranged at a predetermined period (pitch) d2 in the X-direction. The slit 31a and the X-ray phase change portion 31b are each formed so as to extend linearly. The slit 31a and the X-ray phase change portion 31b are each formed so as to extend in parallel with each other. The second grating 31 is a so-called phase grating.

The third grating 32 has a plurality of X-ray transmission portions 32a and a plurality of X-ray absorption portions 32b. The X-ray transmission portion 32a and the X-ray absorption portion 32b are each arranged in the X-direction at a predetermined period (pitch) d3. The X-ray transmission portion 32a and the X-ray absorption portion 32b are each formed so as to extend linearly. The X-ray transmission portion 32a and the X-ray absorption portion 32b are each formed so as to extend in parallel with each other. The second grating 31 is a so-called absorption grating. The first grating 30 and the second grating 31 are gratings with distinct roles, and the slit 31a and the X-ray transmission portion 32a each allow X-rays to pass through. The X-ray absorption portion 32b shields X-rays. Further, the X-ray phase change portion 31b changes the phase of X-rays by the difference of the refractive index between the X-ray phase change portion 31b and the slit 31a.

(Second Grating Group)

As shown in FIG. 2, the first grating 40 has a plurality of slits 40a and a plurality of X-ray absorption portions 40b which are arranged at a predetermined period (pitch) d4 in the Y-direction. The first grating 40 has the same configuration as the first grating 30 except that the extending direction of the grating is arranged differently. That is, the slit 40a and the X-ray absorption portion 40b have the same configuration as the X-ray transmission portion 30a and the X-ray absorption portion 30b.

The second grating 41 has a plurality of slits 31a and a plurality of X-ray phase change portions 31b. Each slit 31a and each X-ray phase change portion 31b are arranged at a predetermined period (pitch) d5 in the Y-direction. The second grating 41 has the same configuration as the second grating 31 except that the extending direction of the grating is arranged differently. That is, the slit 41a and the X-ray phase change portion 41b are the same configuration as the slit 31a and the X-ray phase change portion 31b.

The third grating 42 has a plurality of X-ray transmission portions 42a and a plurality of X-ray absorption portions 42b. The X-ray transmission portion 42a and the X-ray absorption portion 42b are each arranged in the Y-direction at a predetermined period (pitch) d6. The third grating 42 has the same configuration as the third grating 32 except that the extending direction of the grating is arranged differently. That is, the X-ray transmission portion 42a and the X-ray absorption portion 42b have the same configuration as the X-ray transmission portion 32a and the X-ray absorption portion 32b.

In the first embodiment, the first grating group 3 and the second grating group 4 are arranged such that the first direction and the second direction are substantially perpendicular to each other. The X-rays that have passed through the first grating group 3 and the X-rays that have passed through the second grating group 4 are detected by a common detector 2. Further, the first grating group 3 and the second grating group 4 are arranged within the irradiation range of the X-rays irradiated from the common X-ray source 1. The first grating 30 of the first grating group 3 and the first grating 40 of the second grating group 4 are integrally formed by a board RS. The second grating 31 of the first grating group 3 and the second grating 41 of the second grating group 4 are formed separately. The third grating 32 of the first grating group 3 and the third grating 42 of the second grating group 4 are formed separately. Further, each grating of the first grating group 3 and each grating of the second grating group 4 has a flat plate shape.

(Grating Moving Mechanism)

Figure 3:
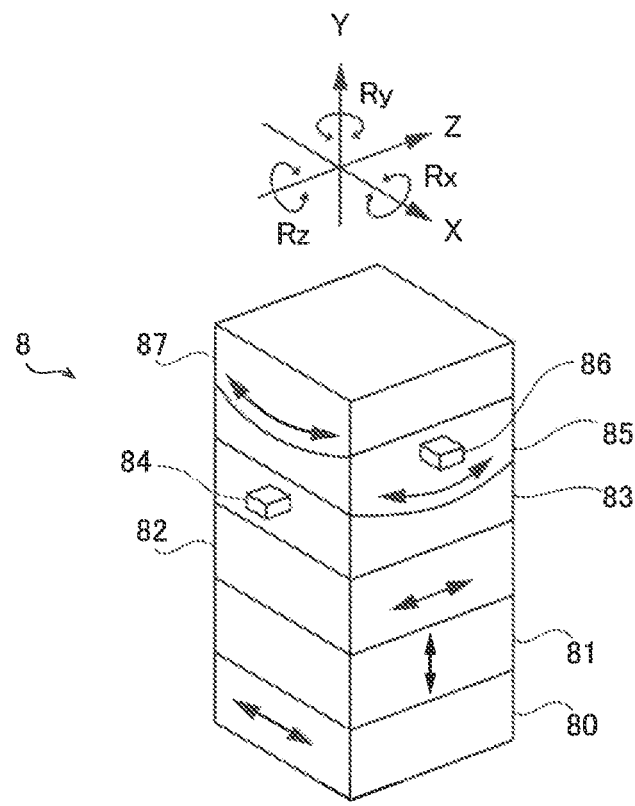
FIG. 3 is a schematic diagram for explaining the configuration of a grating position adjustment mechanism according to the first embodiment.

As shown in FIG. 3, the grating moving mechanism 8 is configured to move the second grating 31 in the X-direction, the Y-direction, the Z-direction, the rotation direction Rz about the axis of the Z-direction, the rotation direction Rx about the axis of the X-direction, and the rotation direction Ry about the axis of the Y-direction. Specifically, the grating moving mechanism 8 is provided with an X-direction linear motion mechanism 80, a Y-direction linear motion mechanism 81, a Z-direction linear motion mechanism 82, a linear motion mechanism connection unit 83, a stage support unit drive unit 84, a stage support unit 85, a stage drive unit 86, and a stage 87. The X-direction linear motion mechanism 80 is configured to be movable in the X-direction. The X-direction linear motion mechanism 80 includes, for example, a motor or the like. The Y-direction linear motion mechanism 81 is configured to be movable in the Y-direction. The Y-direction linear motion mechanism 81 includes, for example, a motor and the like. The Z-direction linear motion mechanism 82 is configured to be movable in the Z-direction. The Z-direction linear motion mechanism 82 includes, for example, a motor or the like.

The grating moving mechanism 8 is configured to move the second grating 31 in the X-direction by the operation of the X-direction linear motion mechanism 80. Further, the grating moving mechanism 8 is configured to move the second grating 31 in the Y-direction by the operation of the Y-direction linear motion mechanism 81. Further, the grating moving mechanism 8 is configured to move the second grating 31 in the Z-direction by the operation of the Z-direction linear motion mechanism 82. Note that the grating moving mechanism 8 is configured to move the second grating 41 in the same manner as the second grating 31. The grating moving mechanism 8 is provided on each of the second grating 31 and the second grating 41 to move the second grating 31 and the second grating 41 independently.

The stage support unit 85 is supporting the stage 87 from the below (in the Y1-direction). The stage drive unit 86 is configured to reciprocate the stage 87 in the X-direction. The bottom portion of the stage 87 is formed in a convex curved surface shape toward the stage support unit 85 and is configured to rotate about the axial line (Rz-direction) of the Z-direction by being reciprocated in the X-direction. The stage support unit drive unit 84 is configured to reciprocate the stage support unit 85 in the Z-direction. The bottom of the stage support unit 85 is formed in a convex curved surface shape toward the linear motion mechanism connection unit 83 and is configured to be rotated about the axis line (Rx-direction) of the X-direction by being reciprocated in the Z-direction direction. The linear motion mechanism connection unit 83 is provided on the X-direction linear motion mechanism 80 so as to be rotatable about the axial line (Ry-direction) of the Y-direction. Thus, the grating moving mechanism 8 can rotate the grating about the central axis of the Y-direction.

In the first embodiment, the X-ray phase imaging system 100 images the subject T with the Moire fringes MFs generated in advance. In the first embodiment, the subject T is moved in the X-direction, which generates a Moire fringe MF in which the periodic direction is in the X-direction. Specifically, the first grating group 3 is arranged so as to extend in the Y-direction. Therefore, in order to produce a Moire fringe MF in which the periodic direction is in the X-direction by the first grating group 3, the second grating 31 is arranged at a position moved to a position moved from a position where no Moire fringe MF is not generated by a predetermined distance. For this reason, in order to produce a Moire fringe MF in which the periodic direction is the X-direction by the second grating group 4, the second grating 41 is arranged in a state of being rotated by a predetermined angle about the Z-direction.

(Generation of Phase-Contrast Image)

Next, referring to FIG. 4 to FIG. 12, the configuration in which the X-ray phase imaging system 100 according to the first embodiment generates a phase-contrast image 14 (see FIG. 12) will be described.

The example shown in FIG. 4 is a schematic diagram of the image 10 captured while continuously straightly moving the subject T by the moving mechanism 5. Specifically, the example shown in FIG. 4 is an example in which the rectangular subject T is continuously imaged while being moved from one side (right side) to the other side (left side) of the imaging range.

As shown in FIG. 4, in the first embodiment, the controller 7 is configured to perform image capturing while moving the subject T in a state in which a Moire fringe MF is generated. In the first embodiment, the controller 7 performs image capturing while moving the subject T in a state in which a Moire fringe MF in which one period a period d7 is generated. Note that in the first grating group 3 and in the second grating group 4, although the method of adjusting the relative position of each grating performed to produce a Moire fringe MF differs, the first grating group 3 and the second grating group 4 are arranged so as to produce a Moire fringe MF in which the periodic direction is the X-direction. Therefore, since the configuration for extracting the phase information 12 of the Moire fringe MF, which will be described later, is the same, the Moire fringe MF generated by the first grating group 3 will be described below.

As shown in FIG. 5, in the first embodiment, the image processing unit 6 is configured to acquire the phase information 12 of the Moire fringe MF. Specifically, the X-ray phase imaging system 100 acquires the Moire fringe image 11 in each Step as shown in FIG. 5 by translating the second grating 31 by the grating moving mechanism 8. The image processing unit 6 is configured to acquire the phase information 12 of the Moire fringe MF based on each Moire fringe image 11. Specifically, the Moire fringe image 11 in the first to fourth Steps of FIG. 5 is defined as $I_k(x, y)$, and $S(x, y)$ is defined as shown in the below Expression (1).

$$S(x, y) = \sum_{k=1}^{M} I_k(x, y)\exp\left(-\frac{2i\pi k}{M}\right) \quad (1)$$

where "k" is the number of each Step. "M" is the number of times that the grating is translated. Further, "x" and "y" are pixel positions (coordinates) in the plane orthogonal to the irradiation axis of the X-rays on the detection plane of the detector 2.

Using the above-described Expression (1), the phase information 12 of the Moire fringe MF is represented by the following Expression (2).

$$\varphi(x,y)=\arg[S(x,y)] \quad (2)$$

Here, $\varphi(x, y)$ is the phase information 12 of the Moire fringe MF. In the first embodiment, a sine curve (sine wave) may be used to fit $I_k(x, y)$ as a function of k, and the phase information of the sine curve may be the phase information 12 of the Moire fringe MF. The phase information 12 of the Moire fringe MF is an image of a striped pattern in which the change in the phase value of the Moire fringe MF is repeated every one period d7.

In the first embodiment, the image processing unit 6 is configured to associate the pixel value in each pixel of the subject T in the plurality of images 10 with the phase value of the Moire fringe MF in each pixel, based on a plurality of images 10 captured while relatively moving the phase value T and the imaging system 9 and the phase information 12 of the Moire fringe MF generated in the plurality of images 10 in each of the first grating region R1 and the second grating region R2. Further, the image processing unit 6 is configured to generate a phase-contrast image 14 by performing the aligning the pixel of the subject at the same position in the plurality of images 10 in each of the first grating region R1 and the second grating region R2, based on the position information of the pixel of the subject T at the same position in the plurality of images 10 and the pixel value of each pixel associated with the phase value.

In the first embodiment, the image processing unit 6 is configured to generate the position calibration data for use in the alignment of the pixel of the subject T at the same position in the plurality of images 10, based on the plurality of position calibration images 13 (see FIG. 6) captured while relatively moving the marker M and the imaging system 9. The marker M may be anything as long as it absorbs X-rays. In the first embodiment, the marker M includes, for example, a wire or the like.

(Generation of Position Calibration Data)

Figure 6:
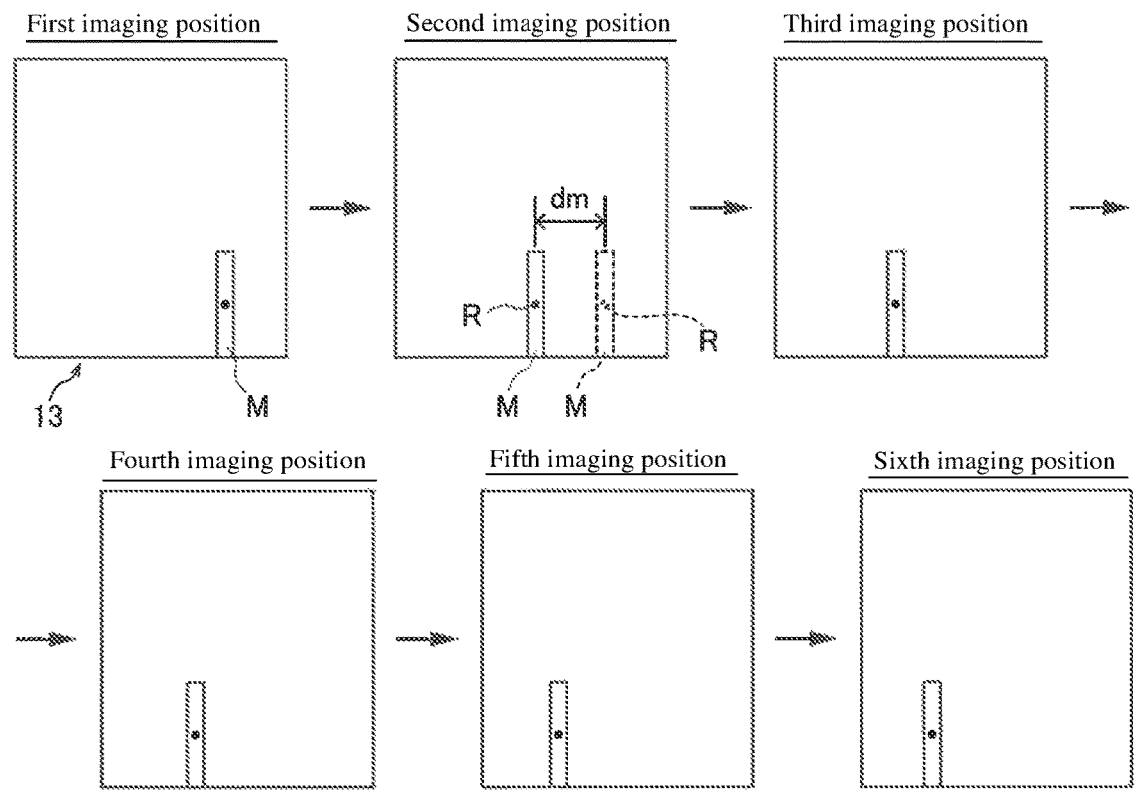
FIG. 6 is a schematic diagram of a plurality of position calibration images captured by the X-ray phase imaging system according to the first embodiment.

FIG. 6 is a schematic diagram of a position calibration image 13 captured while moving the marker M in the X-direction by the moving mechanism 5. The position calibration image 13 shown in FIG. 6 is an example of an image captured while moving the marker M to the first imaging position to the sixth imaging position. Further, in the example shown in FIG. 6, among the pixels reflecting the marker M, the movement amount dm of the marker M is acquired by focusing on the pixel R.

The position calibration data is generated, based on the command value related to a movement amount input to the moving mechanism 5 when relatively moving the marker M and the imaging system 9 by the moving mechanism 5 and the actual movement amount dm of the marker M in the position calibration image 13 when the marker M and the imaging system 9 are relatively moved based on the command value. Specifically, the position calibration data is generated by acquiring the approximate expression showing the relation between the command value and the movement amount dm of the marker M, based on the position of each pixel of the marker M at the same position in a plurality of position calibration images 13.

Figure 7:
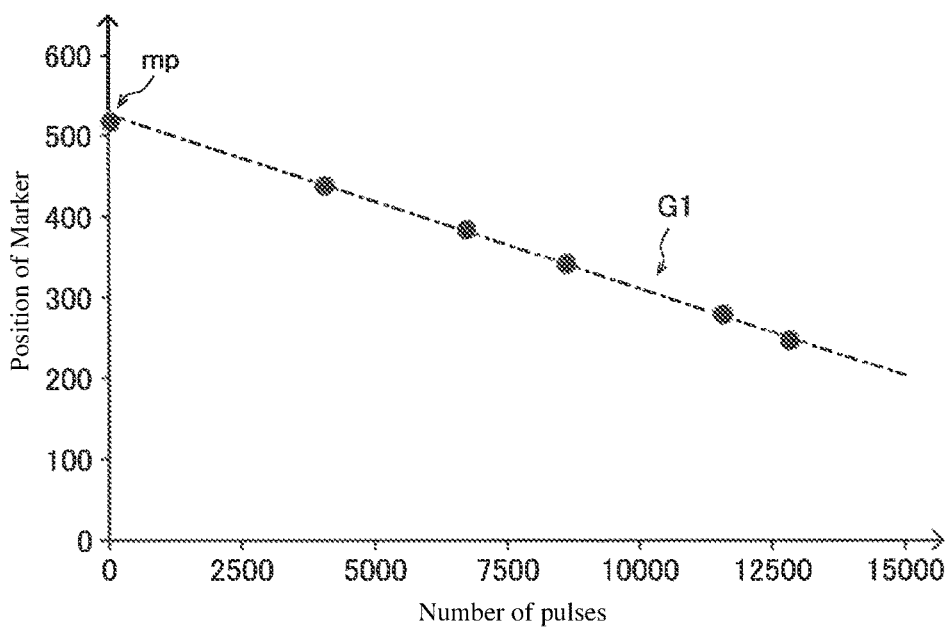
FIG. 7 is a schematic diagram for explaining the acquisition of an approximate expression for acquiring the position calibration data.

FIG. 7 is an example of a graph G1 in which the vertical axis represents the position of the marker M in each position calibration image 13 and the horizontal axis represents the command value when the marker M is moved. The controller 7 acquires an approximate expression by linearly fitting each plot mp shown in the graph G1.

In the first embodiment, the moving mechanism 5 is configured to continuously move the subject T when imaging the subject T. Specifically, the moving mechanism 5 is configured to continuously move the subject T by moving the subject T at a substantially constant velocity while the subject T passes through the first grating region R1 and the second grating region R2. Further, the image processing unit 6 is configured to generate a phase-contrast image 14 based on the acquired sequential image 10. In the first embodiment, the image 10 is acquired as a moving image acquired by continuously capturing the image 10 at a predetermined frame rate.

In the first embodiment, in order to acquire the image 10 as a moving image, the controller 7 acquires the following Expression (3) as the position calibration data.

$$x_i = x_{start} + p1 \times vp \times (1/fps) \times i \quad (3)$$

Where "$x_i$" is a position of a pixel of the subject T at the same position in the $i^{th}$ frame, "$x_{start}$" is a position of a pixel in the first frame among pixels of the subject T at the same position. "vp" is a speed (pulse/s) when the moving mechanism 5 moves the subject T. Further, "fps" is a frame rate (frame/s) when capturing a moving image. Further, "i" is a frame number of a moving image.

Figure 8:
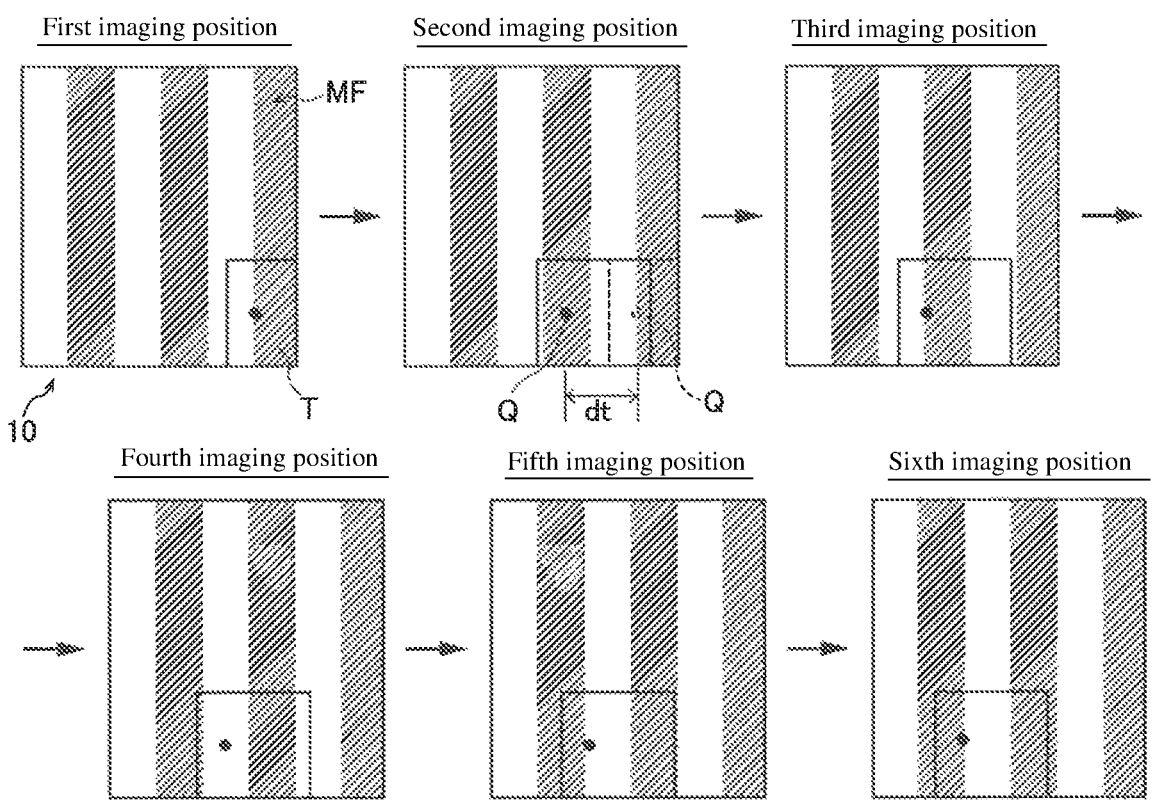
FIG. 8 is a schematic diagram of a plurality of images captured at the first to sixth imaging positions among images continuously captured by the X-ray phase imaging system according to the first embodiment.
Figure 9:
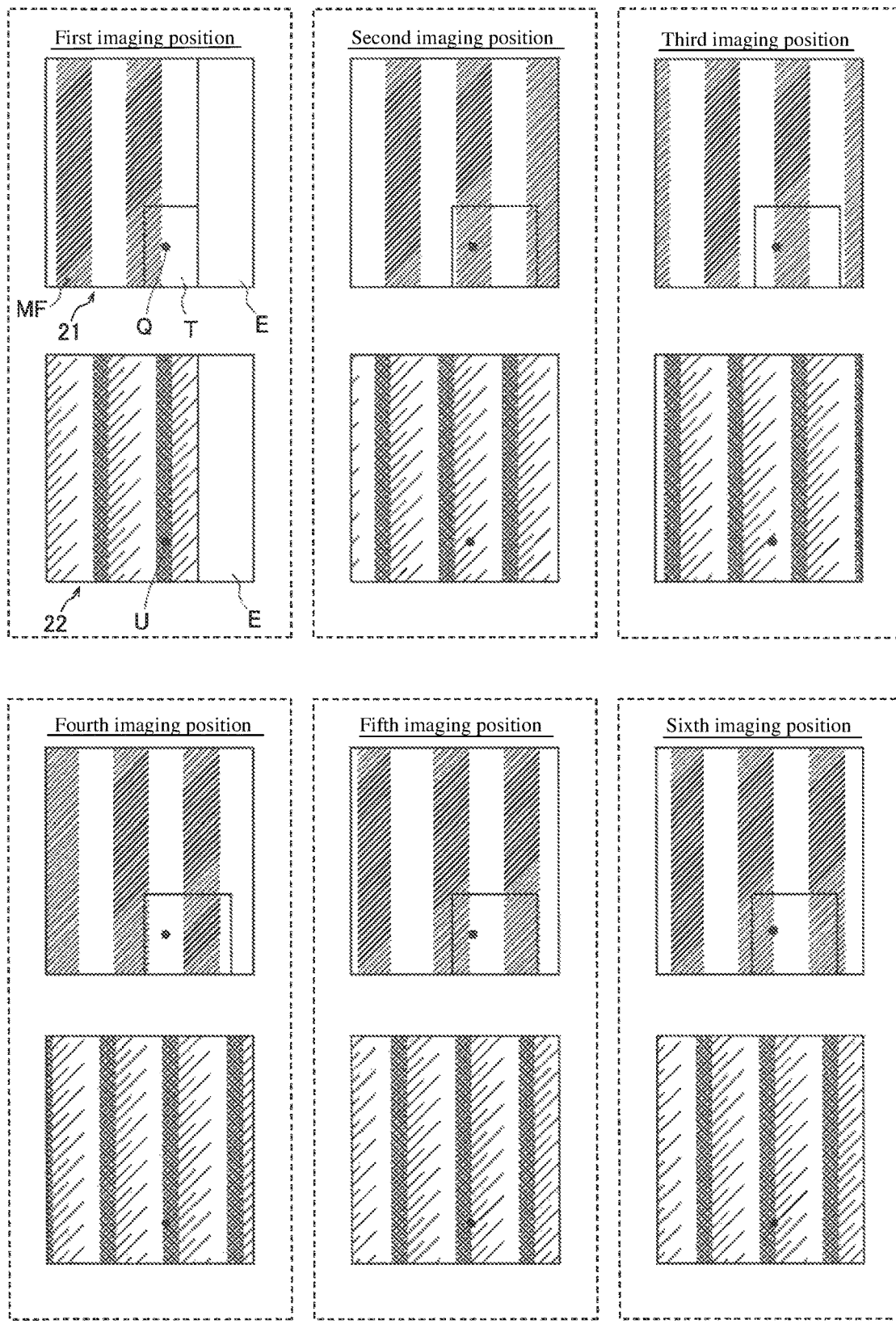
FIG. 9 is a schematic diagram for explaining the alignment of each pixel of the subject at the same position in a plurality of images.

Next, referring to FIG. 8 and FIG. 9, the alignment between the pixel Q in the continuously captured images 10 and the phase information 12 will be described. In FIG. 8 and FIG. 9, for simplicity, among the respective images 10, the description will be made using the images 10 captured when the subject T is arranged at the first imaging position to the sixth imaging position among images 10.

The example shown in FIG. 8 is an example in which imaging is performed at six positions (the first imaging position to the sixth imaging position) while the rectangular subject T is moved from one side (right side) to the other side (left side) of the imaging range by the moving mechanism 5. In the first imaging position, a part of the subject T in the X-direction is not arranged on the detection surface of the detector 2, and therefore in the captured image 10, a part of the subject T is not reflected. Further, the example shown in FIG. 8 is an example showing the change in the position of the pixel Q among the pixels reflecting the subject T in the plurality of images 10. Note that the plurality of images 10 is an example of the "plurality of images captured while relatively moving the subject and the imaging system" recited in claims".

Note that the image 10 at the second imaging position of FIG. 8, in order to facilitate grasping the movement amount dt of the subject T, the position of the subject at the first imaging position is illustrated by a broken line. By performing the imaging while moving the subject T by the moving mechanism 5, it is possible to relatively move the Moire fringe MF and the subject T, so that the image processing unit 6 can generate a phase-contrast image 14. In the second embodiment, the subject T is moved by at least one period d7 (see FIG. 4) of the Moire fringe MF by the moving mechanism 5.

In the first embodiment, the image processing unit 6 acquires the position in each image 10 of the pixel of the subject T at the same position using the position calibration data and performs the alignment of the pixel in each image 10. Specifically, as shown in FIG. 9, the alignment between each image 10 and the phase information 12 is performed, and the aligned subject image 21 and phase information 22 are acquired.

The example shown in FIG. 9 shows performed subject images 21 in which the respective images 10 at the first imaging position to the sixth imaging position are aligned at the second imaging position when acquiring the aligned alignment and phase information 22. Note that in the image captured by arranging the subject T in the first imaging position, since the entire subject T in the X-direction is not reflected, a blank region E is occurring in the subject image 21 after the alignment. In each subject image 21 after the alignment, when focusing on the pixel Q, it is understood that the Moire fringe MF has been moved with respect to the pixel Q. In the example shown in FIG. 9, the position corresponding to the position of the pixel Q of each subject image 21 after the alignment is illustrated by a point U. That is, the position of the pixel at each imaging position and the position of the phase value of the Moire fringe MF in the phase information 22 after the alignment correspond in a one-to-one relation.

Figure 10:
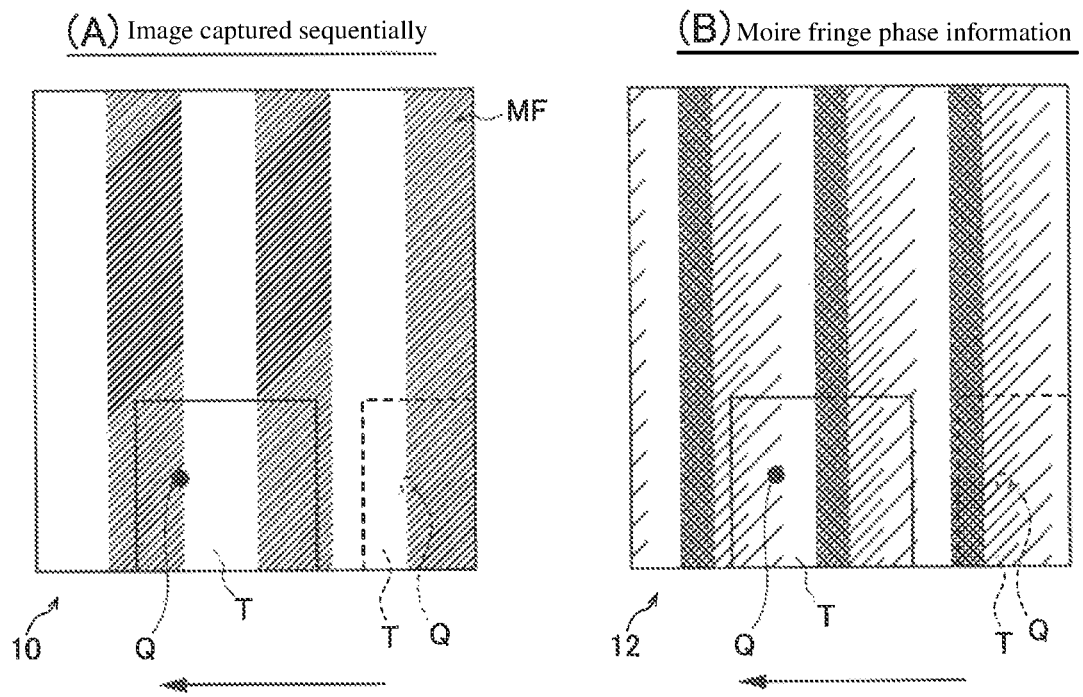
FIG. 10 is a schematic diagram for explaining the alignment between each pixel of the subject and the phase information of the Moire fringe in the continuously captured images.

In the first embodiment, for each frame of the image 10 acquired as a moving image, the alignment with the phase information 12 is performed, and the aligned subject image 21 and phase information 22 are acquired. That is, as shown in FIG. 10, the pixel of each frame of the continuously captured image 10 and the phase information 12 are aligned using position calibration data.

Figure 11:
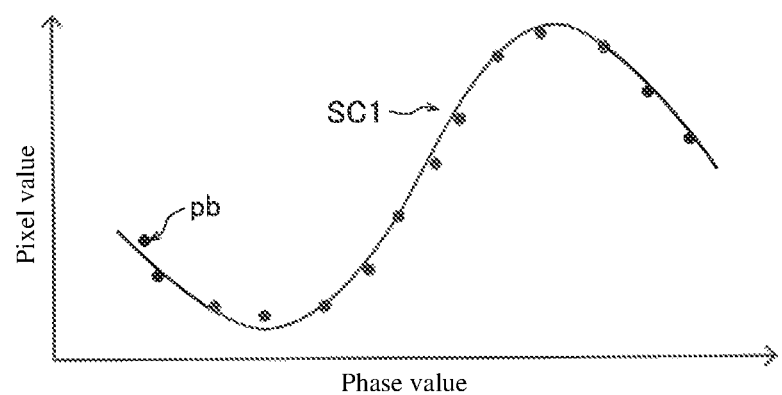
FIG. 11 is a schematic diagram of an intensity signal curve acquired by associating each phase value and each pixel value of each pixel of continuously captured images by the first embodiment in a one-to-one relation.

The image processing unit 6 associates the pixel value of each pixel of the image 10 with the phase value of the Moire fringe MF, based on the pixel of the image 10 acquired as a moving image and the phase information 12, and acquires the intensity signal curve SC1 shown in FIG. 11. The intensity signal curve SC1 is a graph in which the horizontal axis represents the phase value and the vertical axis represents the pixel value. In the first embodiment, the image processing unit 6 generates the phase-contrast image 14 based on the intensity signal curve SC1. Note that for the blank region E shown in FIG. 9, since there is no phase information 12 of the Moire fringe MF, no sampling is performed in FIG. 11.

Figure 12:
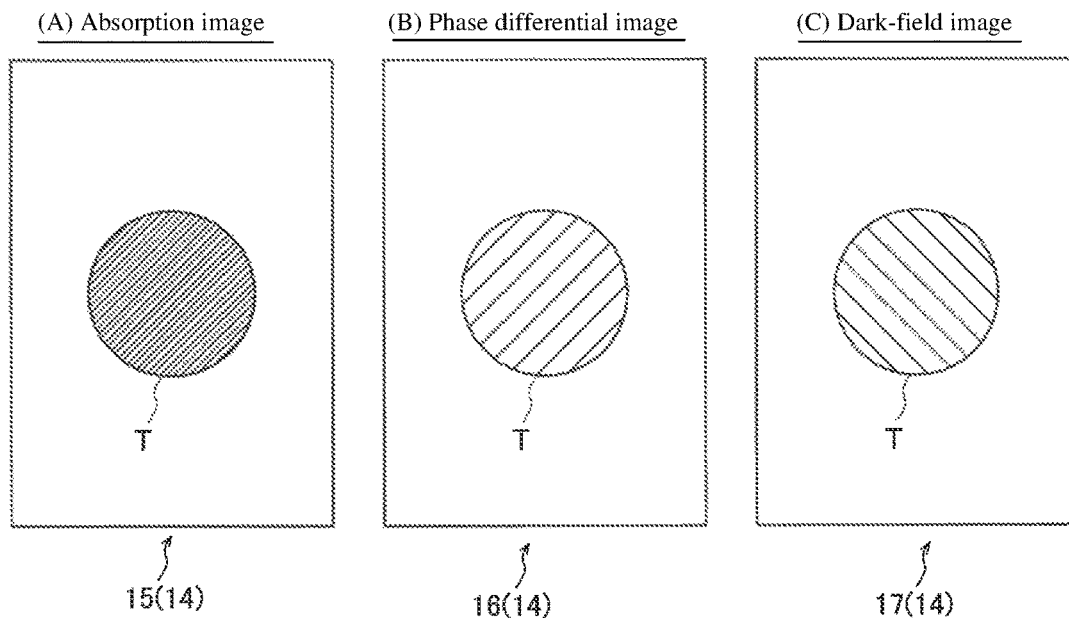
FIG. 12 is a schematic diagram of an absorption image (A), a phase differential image (B), and a dark-field image (C) generated by the image processing unit according to the first embodiment.

FIG. 12 is a schematic diagram of phase-contrast images 14. In the first embodiment, the image processing unit 6 generates an absorption image 15, a phase differential image 16, and a dark-field image 17, based on the acquired intensity signal curve SC1. The method of generating the absorption image 15, the phase differential image 16, and the dark-field image 17 can be performed by a known method, and therefore the explanation thereof is omitted.

In the first embodiment, the image processing unit 6 and the controller 7 are configured to acquire the intensity signal curve SC1 from the image 10 captured in the second grating region R2, similarly to the generation of the phase-contrast image 14 captured in the first grating region R1. Further, the image processing unit 6 and the controller 7 is configured to generate a phase-contrast image 14 in the second grating region R2, based on the intensity signal curve SC1 acquired in the second grating region R2.

(First Composite Image)

Figure 13:
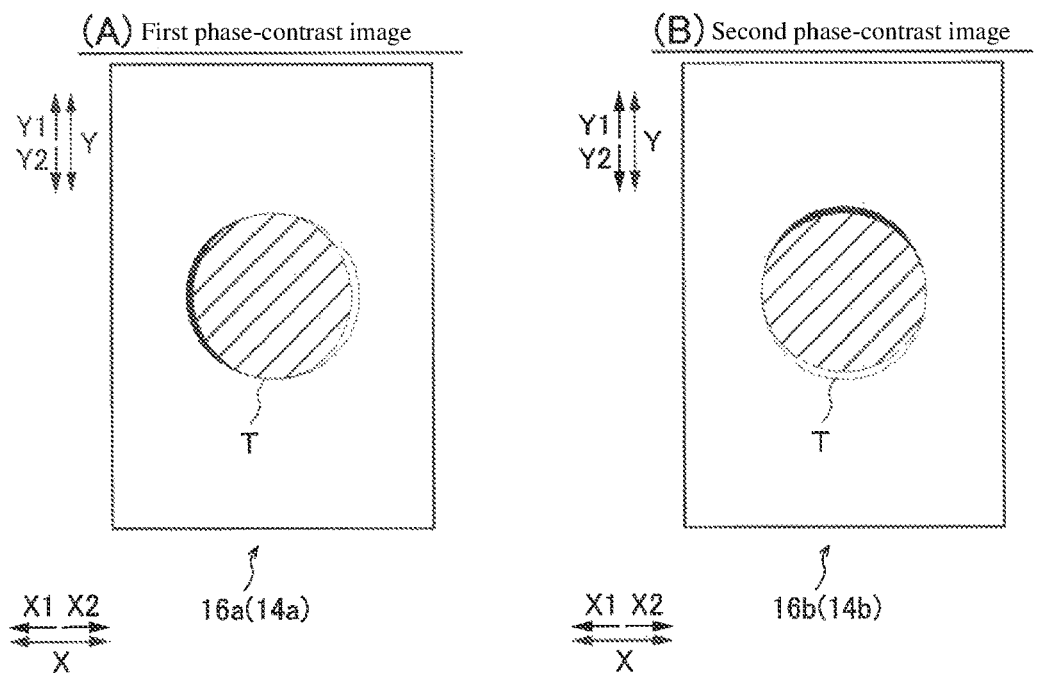
FIG. 13 is a schematic diagram (A) of the first phase-contrast image and a schematic diagram (B) of the second phase-contrast image generated by the image processing unit according to the first embodiment.

The example shown in (A) of FIG. 13 shows a schematic diagram of the first phase differential image 16a captured when the subject has passed through the first grating region R1. (B) of FIG. 13 shows a schematic diagram of the second phase differential image 16b captured when the subject has passed through the second grating region R2. In the phase differential image 16, the direction of the edge to be emphasized differs in the first phase differential image 16a and the second phase differential image 16b because the grating is sensitive in a direction perpendicular to the extending direction. That is, in the first phase differential image 16a, the edge in a direction (X-direction) perpendicular to the first direction (Y-direction) is emphasized. In the second phase differential image 16b, the edge in a direction (Y-direction) perpendicular to the second direction (X-direction) is emphasized.

In the first embodiment, the image processing unit 6 is configured to generate a first composite image 19 (see FIG. 15) in which the first phase-contrast image 14a and the second phase-contrast image 14b are composed. Specifically, the image processing unit 6 is configured to generate a phase image 18 (first composite image 19) based on the first phase differential image 16a (the first phase-contrast image 14a) when the subject T has passed through the first grating region R1 and the second phase differential image 16b (second phase-contrast image 14b) when the subject T has passed through the second grating region R2.

Figure 14:
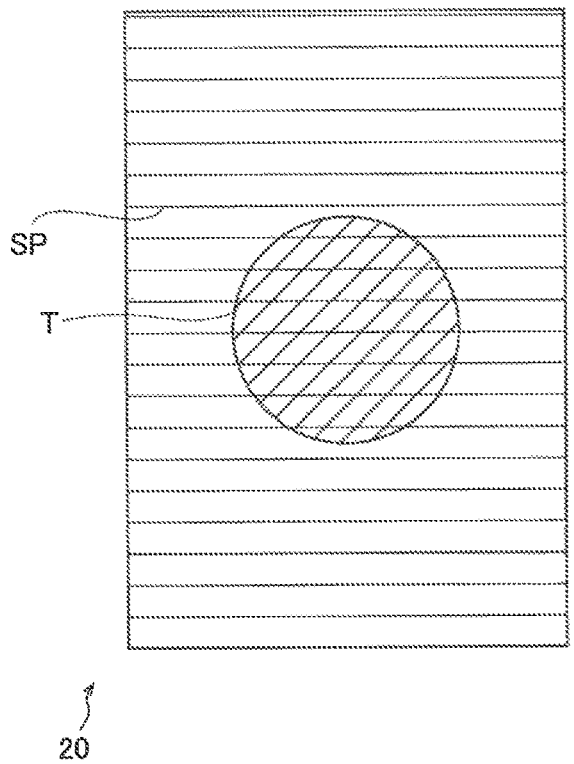
FIG. 14 is a schematic diagram for explaining a phase image according to a Comparative Example.

FIG. 14 is a schematic diagram of a phase image 20 according to a reference example. In the example shown in FIG. 14, a phase image 20 is generated using a phase differential image having sensitivity in the X-direction or Y-direction. Specifically, in a phase differential image, the phase image 20 is generated by integrating along the Y-direction (or X-direction) intersecting with the X-direction (or Y-direction) in which the edge is emphasized. In the reference example, however, the phase differential image to be integrated has sensitive only in the Y-direction (or X-direction). Therefore, due to the noise contained in the direction along which there is no sensitivity, artifacts SP occur in the generated phase image 20. Therefore, the image quality of the phase image 20 deteriorates.

Figure 15:
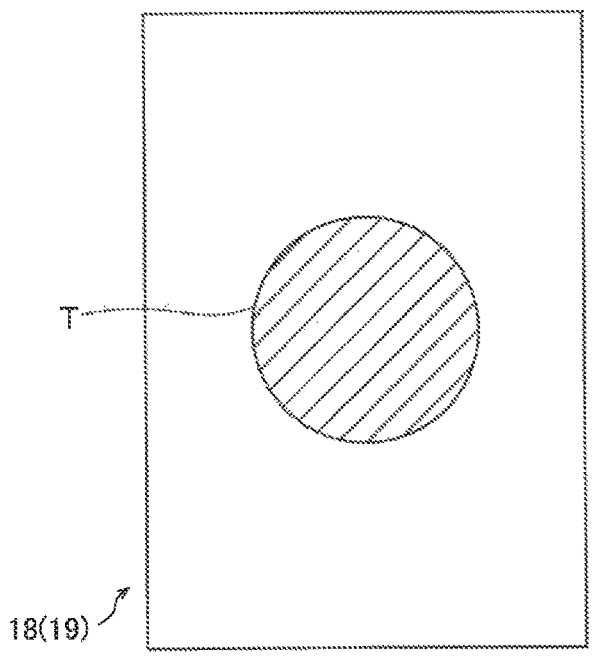
FIG. 15 is a schematic diagram for explaining a phase image generated by the image processing unit according to the first embodiment.

The example shown in FIG. 15 shows a schematic diagram of a phase image 18 generated by the image processing unit 6 according to the first embodiment. The image processing unit 6 generates the phase image 18 by the following Expression (4).

$$\varphi(x, y) = \mathcal{F}^{-1}\left[\frac{\mathcal{F}[\varphi_x + \varphi_y](k, l)}{2\pi i(k + il)}\right](x, y) \quad (4)$$

Where Φx represents the first phase differential image 16a captured in the first grating region R1. Φy represents the first phase differential image 16a captured in the second grating region R2. Also, x and y represent the x-coordinate and the y-coordinate of pixels in the first phase differential image 16a and the second phase differential image 16b. In addition, i represents an imaginary unit representing a complex number. Also, k and l represent coordinates on a frequency space.

In the first embodiment, the image processing unit 6 generates the phase image 18 by the above-described Expression (4) using the first phase differential image 16a having sensitivity in the X-direction and the second phase differential image 16b having sensitivity in the Y-direction. The image processing unit 6 generates the phase image 18 from the first phase differential image 16a and the second phase differential image 16b which are sensitive in each direction, and therefore it is possible to suppress the occurrence of artifacts SP in the phase image 18.

Figure 16:
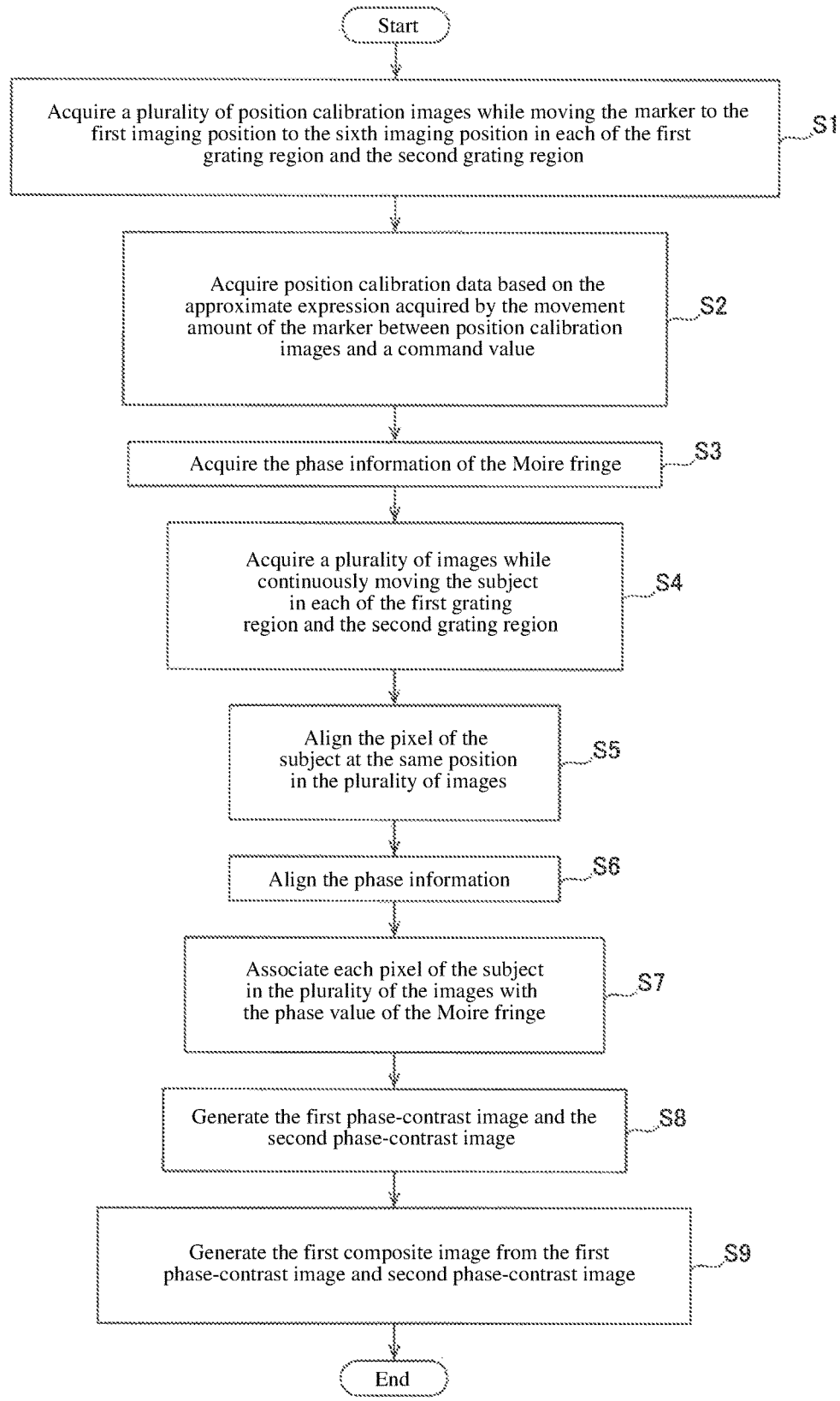
FIG. 16 is a flowchart for explaining the generation processing of a first composite image by the X-ray phase imaging system according to the first embodiment.

Next, referring to FIG. 16, the flow of processing for generating the first phase-contrast image 14a and the second phase-contrast image 14b by the X-ray phase imaging system 100 according to the first embodiment will be described.

In Step S1, the image processing unit 6 acquires a plurality of position calibration images 13 while moving the marker M to the first imaging position to the sixth imaging position in each of the first grating region R1 and the second grating region R2 by the moving mechanism 5 under the control of the controller 7. Next, in Step S2, the controller 7 acquires an approximate expression based on the movement amount dm of the marker M and the command value. The controller 7 acquires the position calibration data based on the inclination of the acquired approximate expression. Thereafter, the processing proceeds to Step S3.

Next, in Step S3, the image processing unit 6 acquires the phase information 12 of the Moire fringe MF. Thereafter, in Step S4, the image processing unit 6 acquires the images 10 while relatively moving the subject T and the imaging system 9 by the moving mechanism 5 in each of the first grating region R1 and the second grating region R2 under the control of the controller 7. Note that in the first embodiment, the moving mechanism 5 continuously moves the subject T. Thereafter, the processing proceeds to Step S5.

Next, in Step S5, the image processing unit 6 performs the alignment of pixels of the subject T at the same position in the images 10. Thereafter, the processing proceeds to Step S6.

In Step S6, the image processing unit 6 performs the alignment of the phase information 12 to acquire phase information 22. Thereafter, in Step S7, the image processing unit 6 acquires an intensity signal curve SC1 by associating the pixel of the subject T in the continuously captured images 10 with the phase value of the Moire fringe MF. Next, in Step S8, the image processing unit 6 generates a first phase-contrast image 14a and a second phase-contrast image 14b, based on the intensity signal curve SC1, Next, in Step S9, the image processing unit 6 generates a first composite image 19 from the first phase-contrast image 14a and the second phase-contrast image 14b, and ends the processing.

The acquisition processing of the position calibration data in Step S1 and Step S2 and the acquisition processing of the phase information 12 of the Moire fringe MFs in Step S3 may be performed by either processing first. The acquisition processing of the position calibration data may be performed at any timing as long as it is prior to the alignment of the pixels in the plurality of images 10. The processing of acquiring the phase information 12 of the Moire fringe MF may be performed at any time as long as it is prior to the processing of performing the alignment of the phase information 12.

(Effects of First Embodiment)

In this first embodiment, the following effects can be obtained.

In the first embodiment, as described above, the X-ray phase imaging system 100 is provided with the X-ray source 1, the detector 2, the first grating group 3, the second grating group 4, the moving mechanism 5, and the image processing unit 6. The detector 2 is configured to detect the X-rays emitted from the X-ray source 1. The first grating group 3 includes a plurality of gratings arranged along the X-ray optical axis XRa direction (Z-direction) between the X-ray source 1 and the detector 2 with the extending direction of the grating being along the first direction (Y-direction). The second grating group 4 includes a plurality of gratings arranged along the Z-direction between the X-ray source 1 and the detector 2. The second grating group 4 is arranged side by side with the first grating group 3 in the direction (X-direction) different from the Y-direction. The moving mechanism 5 is configured to relatively move the subject T and the imaging system 9, the imaging system being composed of the X-ray source, the detector 2, the first grating group 3, and the second grating group 4. The image processing unit 6 is configured to generate the phase-contrast image 14 based on the signal detected by the detector 2. The moving mechanism 5 is configured to relatively move the subject T and the imaging system 9 such that the subject T passes through the first grating region R1 in which the first grating group 3 is arranged and the second grating region R2 in which the second grating group 4 is arranged. The image processing unit 6 is configured to generate the first phase-contrast image 14a when the subject T has passed through the first grating region R1 and the second phase-contrast image 14b when the subject T has passed through the second grating region R2.

With this configuration, by imaging the subject T by passing through the first grating region R1 and the second grating region R2, the subject T can be imaged by the first grating group 3 and the second grating group 4 in which the grating extension directions differ from each other. Consequently, without imaging while moving the subject T again with the orientation of the subject T or the grating changed, it is possible to perform imaging with the orientation of the grating with respect to the subject T changed. Thus, it is possible to simplify the imaging operation and it is also possible to shorten the imaging time.

Further, in the first embodiment, as described above, the first grating group 3 and the second grating group 4 are arranged such that the Y-direction and the second direction (X-direction) are substantially perpendicular. With this, since the first direction (Y-direction) and the second direction (X-direction) are substantially perpendicular, regardless of the arrangement direction of the subject T, in either the first grating group 3 or the second grating group 4, it is possible to extract the X-ray phase shift or the X-ray refraction by the subject T. Consequently, the subject T can be imaged in either the first phase-contrast image 14a or the second phase-contrast image 14b, regardless of the arrangement direction of the subject T.

In the first embodiment, as described above, the image processing unit 6 is configured to generate the first composite image 19 in which the first phase-contrast image 14a and the second phase-contrast image 14b are composed. This makes it possible to collectively grasp the sensitivities in the first direction (Y-direction) and the first direction (Y-direction) in the first composite image 19 in which the second phase-contrast image 14b having the sensitivity in the first direction (Y-direction) and the first phase-contrast image 14a having the sensitivity in the second direction (X-direction) are composed. Consequently, the internal structure of the subject T can be grasped in detail.

In the first embodiment, as described above, the X-rays that have passed through the first grating group 3 and the X-rays that have passed through the second grating group 4 are detected by the common detector 2. Thus, by providing one detector 2, it is possible to detect the X-rays that have passed through the first grating group 3 and the X-rays that have passed through the second grating group 4. Consequently, as compared with the case in which a detector 2 for detecting the X-rays that have passed through the first grating group 3 and a detector 2 for detecting the X-rays that have passed through the second grating group 4 are provided, it is possible to suppress the increase in the number of components.

In the first embodiment, as described above, the first grating group 3 and the second grating group 4 are arranged within the irradiation range of the X-rays emitted from the common X-ray source 1. With this, by providing one X-ray source 1, it is possible to emit X-rays to the first grating group 3 and the second grating group 4. As a result, it is possible to suppress the increase in the number of components as compared with a case in which an X-ray source 1 for irradiating the first grating group 3 with X-rays and an X-ray source 1 for irradiating the second grating group 4 with X-rays are separately provided.

Further, in the first embodiment, as described above, the first grating group 3 and the second grating group 4 each include the first grating 30 and the first grating 40 each for enhancing the coherence of the X-rays emitted from X-ray source 1, the second grating 31 and the second grating 41 each for forming the self-image, and the third grating 32 and the third grating 42 each for interfering with the self-image of the second grating 41 and the self-image of the second grating 41. The first grating 30 of the first grating group 3 and the first grating 40 of the second grating group 4 are integrally formed. The second grating 31 of the first grating group 3 and the second grating 41 of the second grating group 4 are formed separately. The third grating 32 of the first grating group 2 and the third grating 42 of the second grating group 4 are formed separately.

Thus, the first grating 30 of the first grating group and the first grating 40 of the second grating group 4, which are arranged in the vicinity of the X-ray source 1, are integrally formed. Therefore, in the first grating group 3 and the second grating group 4, the distance from the X-ray source 1 to the first grating 30 of the first grating group 3 and the distance from the X-ray source 1 to the first grating 40 of the second grating group 4 can be made substantially equal. Further, for example, when imaging by forming a Moire fringe MF in advance, in the Moire fringe MF by the first grating group 3 and the Moire fringe MF by the second grating group 4, the direction of each Moire fringe MF is required to have a finite component perpendicular to the scanning direction. In the first grating group 3 and the second grating group 4, however, since they are arranged such that the grating extending directions differ from each other, the relative position of each grating for forming a Moire fringe MF differs in the first grating group 3 and the second grating group 4. Therefore, by separately forming the second grating 31 of the first grating group 3 and the second grating 41 of the second grating group 4 and separately forming the third grating 32 of the first grating group 3 and the third grating 42 of the second grating group 4, respectively, each grating of the first grating group 3 and each grating of the second grating group 4 can be arranged at a relative position suitable for forming a Moire fringe MF.

Further, for example, in order to acquire the phase information 12 of a Moire fringe MF formed in advance, in a case where imaging is performed while translating the second grating 31 and the second grating 41 or the third grating 32 and the third grating 42 in each of the first grating group 3 and the second grating group 4, the first grating group 3 and the second grating group 4 are arranged such that the grating extending directions differ to each other, the direction of translating the grating differs between the first grating group 3 and the second grating group 4. By separately forming the second grating 31 of the first grating group 3 and the second grating 41 of the second grating group 4 from each other, and by separately forming the third grating 32 of the first grating group 3 and the third grating 42 of the second grating group 4, it becomes possible to provide the moving mechanism 5 on the grating to be translated among the gratings of the first grating group 3 and the second grating group 4. Therefore, it is possible to perform imaging while translating the grating to be translated in different directions in the first grating group 3 and the second grating group 4.

Further, in the first embodiment, as described above, the image processing unit 6 is configured to generate the first phase-contrast image 14a and the second phase-contrast image 14b by associating the pixel value in each pixel of the subject T in the plurality of images 10 with the phase value of the Moire fringe MF in each pixel, based on the plurality of images 10 captured while relatively moving the subject T and the imaging system 9 and the phase information 22 of the Moire fringe MF generated in the plurality of images 10, in each of the first grating region R1 and the second grating region R2, and by aligning the pixels of the subject T at the same position in the plurality of images 10, based on the position information of the pixels of the subject T at the same position in the plurality of images 10 and the pixel value of each pixel associated with the phase value, in each of the first grating region R1 and the second grating region R2. Thus, it is possible to generate the first phase-contrast image 14a and the second phase-contrast image 14b by associating the pixel value of the pixel of the subject T at the same position in each image with each phase value corresponding to the pixel of the subject T at the same position in each image. Thus, it is possible to generate the first phase-contrast image 14a and the second phase-contrast image 14b using the pixel value of each pixel reflecting the same position, as compared with the case in which, for example, the first phase-contrast image 14a and the second phase-contrast image 14b are generated by dividing the one periodic region of the Moire fringe MF and using the average value of the pixel values included in each divided region. Consequently, it is possible to suppress the deterioration of the image quality of the first phase-contrast image 14a and the second phase-contrast image 14b due to the occurrence of errors in the pixel value used in generating the first phase-contrast image 14a and the second phase-contrast image 14b.

Further, in the first embodiment, as described above, the moving mechanism 5 is configured to continuously move the subject T when imaging the subject T. The image processing unit 6 is configured to generate the first phase-contrast image 14a and the second phase-contrast image 14b, based on the acquired continuous images 10. With this, when generating the continuous first phase-contrast image 14a and second phase-contrast image 14b, for example, unlike a conventional fringe scanning method of generating a continuous first phase-contrast image 14a and second phase-contrast image 14b by repeating the movement and imaging of the subject T, it is possible to generate a continuous first phase-contrast image 14a and second phase-contrast image 14b by performing imaging while continuously moving the subject T. As a result, the image capturing time can be shortened as compared with the conventional fringe scanning method.

Further, in the first embodiment, as described above, the image processing unit 6 is configured to generate the position calibration data used for the alignment of each pixel of the subject T at the same position in the plurality of images 10, based on the plurality of position calibration images 13 captured while relatively moving the marker M and the imaging system 9. With this, by using the position calibration data, it becomes possible to acquire the position of the pixel of the subject T at the same position in each image, and therefore it is possible to calculate the movement amount dm of the subject T. Consequently, for example, even in a case where the movement amount dm of the subject T and the movement amount dm of the marker M are not the same, it is possible to acquire the movement amount dm of the subject T. Therefore, it is possible to perform the alignment of each pixel of the subject T at the same position.

Further, in the first embodiment, as described above, the position calibration data is generated based on the command value related to the movement amount dm input to the moving mechanism 5 when relatively moving the marker M and the imaging system 9 by the moving mechanism 5 and the movement amount dm of the marker M or the imaging system 9 in the position calibration image 13 when the marker M and the imaging system 9 have been moved relative to each other based on the command value. With this, even in a case where an error occurs between the command value related to the movement amount dm input to the moving mechanism 5 and the movement amount dm of the marker M or the imaging system 9, the accurate movement amount dm can be acquired by the position calibration data. As a result, since it becomes possible to accurately perform the alignment of the pixel of the subject T at the same position in the plurality of images 10, it is possible to further suppress the deterioration of the image quality of the resulting phase-contrast image 14.

Further, in the first embodiment, as described above, the position calibration data is generated by acquiring the approximate expression showing the relation between the command value and the movement amount dm of the marker M or the imaging system 9, based on the position of each pixel of the marker M at the same position in the plurality of position calibration image 13. Thus, by acquiring the position calibration image based on the position of each pixel of the marker M at the same position in the plurality of position calibration image 13, the relation between the command value related to the movement amount dm to the position different from the position where the plurality of position calibration images 13 is acquired and the movement amount dm of the marker M or the imaging system 9. Consequently, for example, even in a case where the subject T is moved to a position different from the position where the marker M or the imaging system 9 is moved when imaging the subject T, the movement amount dm of the subject T can be acquired.

Further, in the first embodiment, as described above, the image processing unit 6 is configured to generate the phase image 18, based on the first phase differential image 16a (first phase-contrast image 14a) when the subject T has passed through the first grating region R1 and the first phase differential image 16a (second phase-contrast image 14b) when the subject T has passed through the second grating region R2. This makes it possible to suppress the occurrence of artifacts SP in the integration direction in the phase image 20 (first composite image 19), as compared with the configuration in which the phase image 18 is generated by integrating in a predetermined direction in one of the images of the first phase differential image 16a (first phase-contrast image 14a) when the subject T has passed through the first grating region R1 and the first phase differential image 16a (first phase-contrast image 14a) when the subject T has passed through the second grating region R2. As a result, it is possible to suppress the degradation of the image quality of the phase image 20 (first composite image 19).

Second Embodiment

Next, with reference to FIG. 1, FIG. 8, FIG. 9, and FIG. 17, an X-ray phase imaging system 200 (see FIG. 1) according to a second embodiment will be described. Unlike the first embodiment in which imaging is performed while continuously moving the subject T, in the second embodiment, the moving mechanism 5 is configured to move the subject T by a predetermined distance dt (see FIG. 8) at a time when imaging the subject T. The image processing unit 60 (see FIG. 1) is configured to generate a first phase-contrast image 14a and a second phase-contrast image 14b, based on the image 10 acquired while moving the subject by a predetermined distance dt at a time. Note that the same component as that of the above-described first embodiment is denoted by the same reference symbol, and the description thereof is omitted.

(Configuration of X-Ray Phase Imaging System)

First, referring to FIG. 1, the configuration of the X-ray phase imaging system 200 according to the second embodiment will be described.

In the second embodiment, the X-ray phase imaging system 200 has a configuration similar to that of the above-described first embodiment, except that it is provided with an image processing unit 60 and a controller 70. The moving mechanism 5 is configured to move the subject T by a predetermined distance dt (see FIG. 8) at a time when imaging the subject T under the control of the controller 70. The image processing unit 60 is configured to generate a first phase-contrast image 14a and a second phase-contrast image 14b, based on the image 10 acquired while moving the subject by a predetermined distance dt at a time.

In the second embodiment, the imaging is performed by moving the subject T to each position of the first imaging position (see FIG. 8) to the sixth imaging position (see FIG. 8) by the moving mechanism 5. In the second embodiment, the controller 70 moves the subject T by a predetermined movement amount dt by inputting a command value related to the movement amount for placing the subject T to each imaging position to the moving mechanism 5. The command value related to the movement amount is, for example, the number of pulses input to the moving mechanism 5 in a case where the moving mechanism 5 includes a stepping motor as a drive source. It should be noted that the configuration for performing the alignment of each image 10 and the phase information 12 is the same as that of the above-described first embodiment, and therefore the detailed descriptions thereof are omitted.

In the second embodiment, the controller 70 acquires the following Expression (5) as the position calibration data.

$$x = x_{start} + p1 \times np \quad (5)$$

where x is the position in each image of the pixel of the subject T at the same position. $x_{start}$ is the position of the pixel at the first imaging position, among pixels of the subject T at the same position. p1 is a slope of the approximate expression. Further, np is a command value (the number of pulses) to be input to the moving mechanism 5 when moving the subject T.

In the second embodiment, the image processing unit 60 acquires the intensity signal curve SC2 (see FIG. 17) showing the relation between the phase value and the pixel value for the pixel in each subject image 21 (see FIG. 9) after the alignment.

Figure 17:
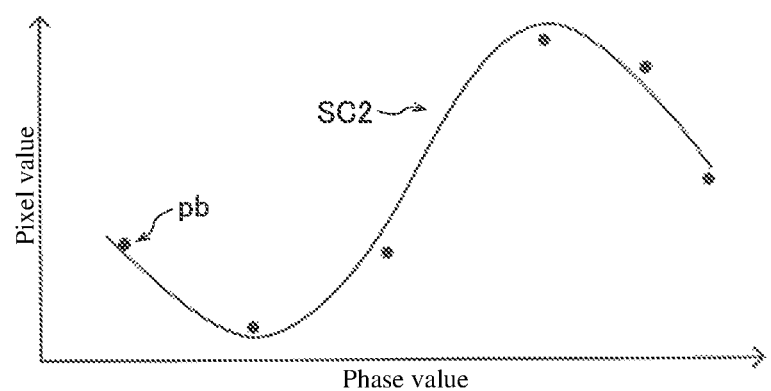
FIG. 17 is a schematic diagram of an intensity signal curve acquired by associating each phase value and each pixel value of each pixel in a plurality of images according to the second embodiment in a one-to-one relation.

The intensity signal curve SC2 shown in FIG. 17 is a graph in which the horizontal axis represents the phase value and the vertical axis represents the pixel value, similarly to the graph of the intensity signal curve SC1 in the first embodiment. The image processing unit 60 acquires the intensity signal curve SC2 of the pixel value in which each phase value and each pixel value of the pixel of the subject T at the same position in a plurality of subject images 21 are associated in a one-to-one relation, by using each subject image 21 after the alignment and the phase information 22 (see FIG. 9). The configuration in which the image processing unit acquires the intensity signal curve SC2 is the same as that in the above-described first embodiment, and therefore the detailed descriptions thereof are omitted. The image processing unit 60 is configured to generate the phase-contrast image 14, based on the acquired intensity signal curve SC2. Note that the blank region E shown in FIG. 9 is not sampled in FIG. 17 in the second embodiment in the same manner as in the first embodiment since there is no phase information 12 of the Moire fringe MF.

Figure 18:
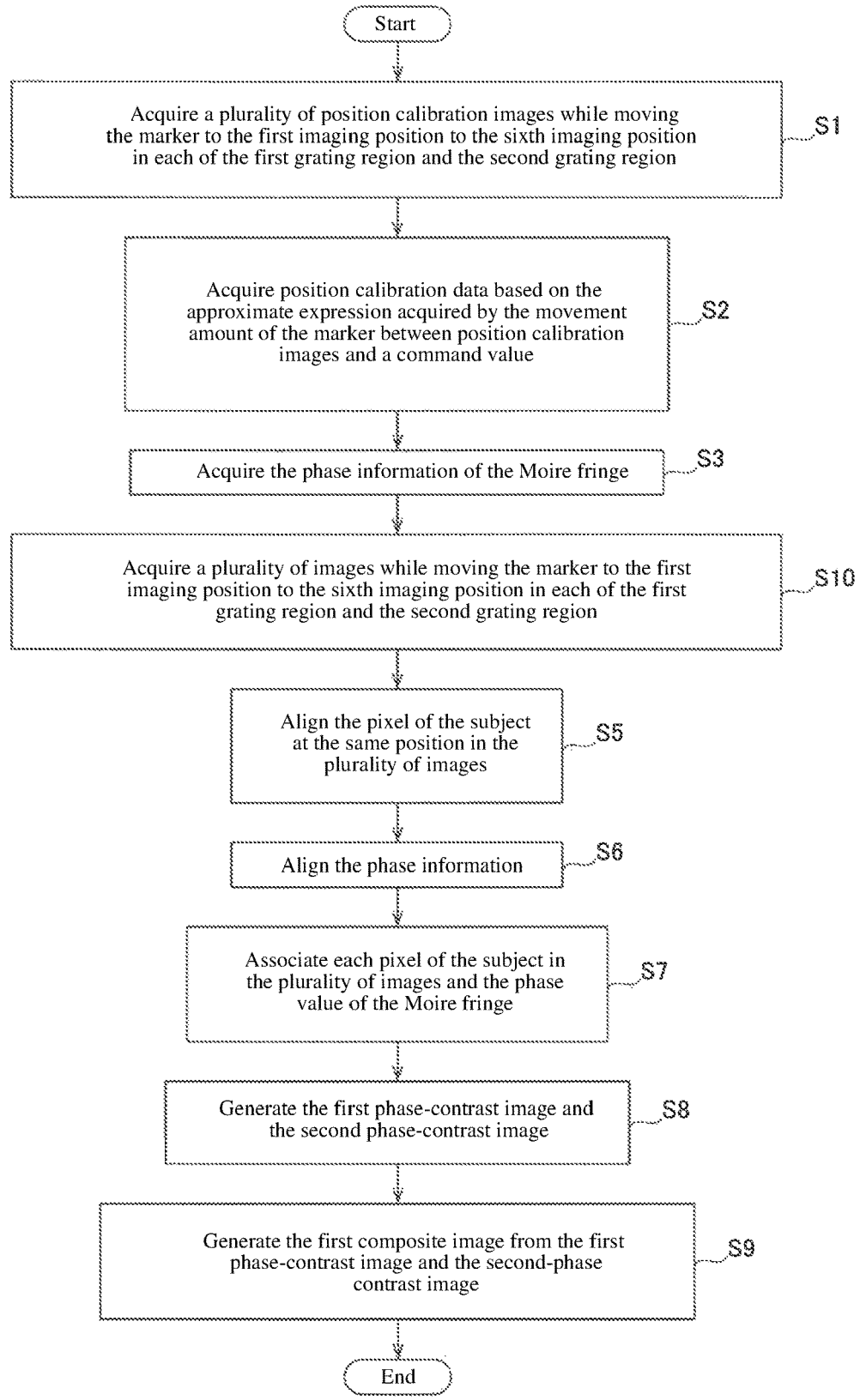
FIG. 18 is a flowchart for explaining the generation processing of a first composite image by the X-ray phase imaging system according to the second embodiment.

Next, referring to FIG. 18, the flow of processing for generating a phase-contrast image 14 by the X-ray phase imaging system 200 according to the second embodiment of the present invention will be described. Note that the description of the same Step as in the first embodiment will be omitted.

In Step S1 to Step S3, the controller 70 acquires the position calibration data and the phase information 12 of the Moire fringe MF. Thereafter, the processing proceeds to Step S10.

In Step S10, the image processing unit 60 acquires a plurality of images 10 while relatively moving the subject T and the imaging system 9 by the moving mechanism 5 under the control of the controller 70. Note that in the first embodiment, the moving mechanism 5 moves the subject T from the first imaging position to the sixth imaging position.

Thereafter, the processing proceeds from Step S5 to Step S9, and the image processing unit 60 generates a first composite image 19, and terminates the processing.

Note that the rest of the configuration of the second embodiment is the same as that of the first embodiment.

(Effects of Second Embodiment)

In this second embodiment, the following effects can be obtained.

In the second embodiment, as described above, the moving mechanism 5 is configured to move the subject T by a predetermined distance dt at a time when imaging the subject T. The image processing unit 60 is configured to generate the first phase-contrast image 14a and the second phase-contrast image 14b, based on the image 10 acquired while moving the subject by a predetermined distance dt at a time. With this, as compared with the case of performing imaging while continuously moving the subject T, it is possible to reduce the number of images 10 when generating the first phase-contrast image 14a and the second phase-contrast image 14b. As a result, the imaging time can be further shortened. In addition, for example, in the case of being used in medical applications, it is possible to suppress the increase in the amount of exposure.

Note that the other effects of the second embodiment are the same as those of the above-described first embodiment.

Third Embodiment

Next, referring to FIG. 19 to FIG. 22, an X-ray phase imaging system 300 (see FIG. 19) according to a third embodiment of the present invention will be described.

Unlike the first and second embodiments described above in which the phase-contrast image 14 including all tomographic planes FP (see FIG. 20) as the imaging targets is generated from a plurality of images 10 in the first grating region R1 and the second phase-contrast image region R2, the X-ray phase imaging system 300 according to the third embodiment is configured to generate the first phase-contrast image 14a and the second phase-contrast image 14b of a predetermined tomographic plane FP as the imaging target. Note that the same configurations as those of the first and second embodiments are denoted by the same reference symbols, and the descriptions thereof will be omitted.

Figure 19:
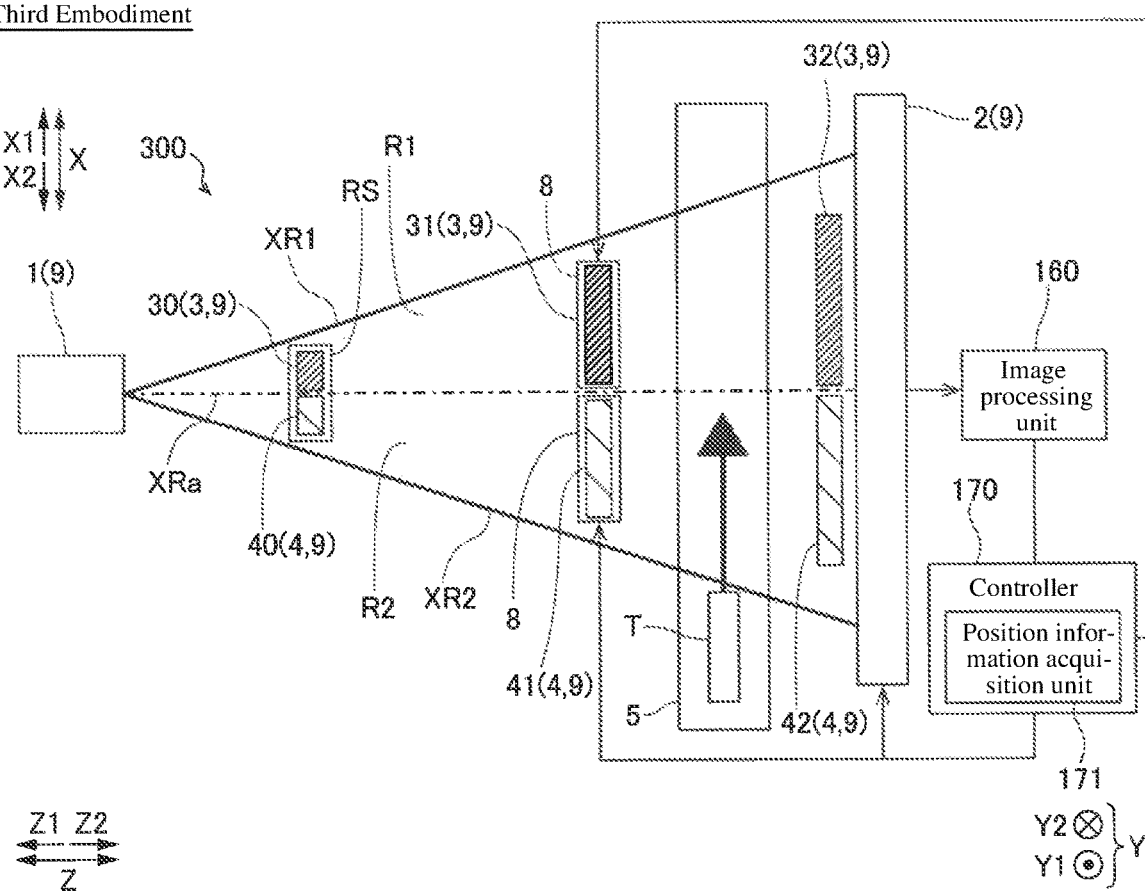
FIG. 19 is a schematic diagram showing the entire configuration of an X-ray phase imaging system according to a third embodiment.

As shown in FIG. 19, the X-ray phase imaging system 300 according to the third embodiment has the same configuration as the X-ray phase imaging system 100 according to the above-described first embodiment except that it is provided with a controller 170 and an image processing unit 160. The controller 170 includes a position information acquisition unit 171.

In the third embodiment, the X-ray phase imaging system 300 is further provided with a position information acquisition unit 171 for acquiring the tomographic position of the tomographic plane FP as an imaging target in the optical axis XRa direction (Z-direction). The image processing unit 160 is configured to generate a first phase-contrast image 14a and a second phase-contrast image 14b in the tomographic plane FP by acquiring the phase distribution in the tomographic plane FP, based on the plurality of images 10 in which the subject T was imaged at a plurality of relative positions with the imaging system 9 and the subject T in a predetermined direction (X-direction) and the acquired tomographic position.

Figure 20:
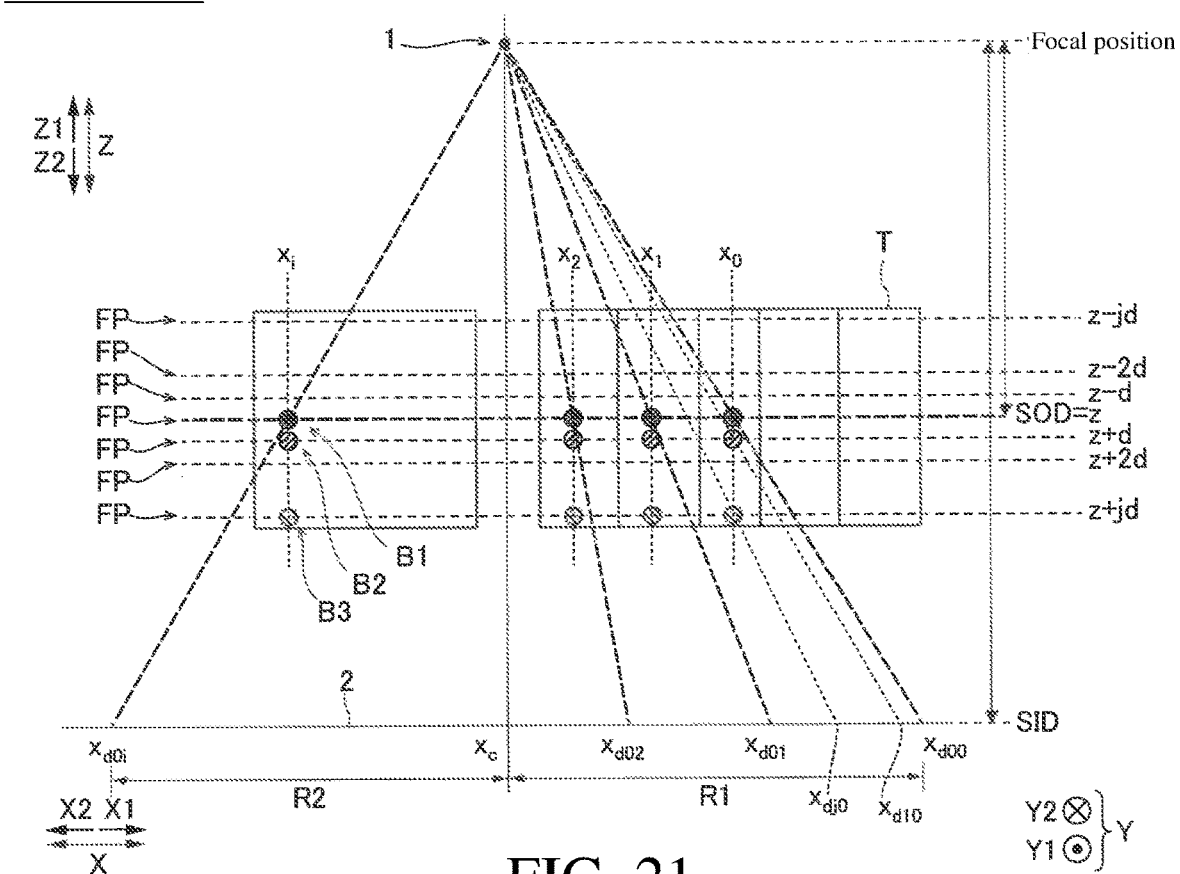
FIG. 20 is a schematic diagram for explaining a relation between a relative position between an imaging system and a subject and a position coordinate in an X-ray image to be captured.

FIG. 20 is a diagram illustrating the relation between the subject T and the position coordinate of the image 10 when capturing the X-ray image at the plurality of relative positions as described above. In FIG. 20, the vertical axis represents the position in the Z-direction, and the horizontal axis represents the position in the predetermined direction (X-direction). In the Z-direction, the focal position of the X-ray source 1 is defined as the origin. As the position in the Z-direction, the position away from the focal point to the center position of the subject T by the distance SOD (source object distance) is referred to as a reference position (hereinafter, referred to as "SOD"). The position away from the focal point by the distance to the detection surface of the detector 2 is defined as a detection surface position SID (source image distance). In FIG. 20, for convenience, the Z-direction is illustrated as an up-down direction on the paper.

In the third embodiment, the tomographic position of the tomographic plane FP of the subject T is expressed as a deviation from the reference position SOD. In FIG. 20, 2j+1 pieces of tomographic planes FP (including the tomographic plane at the reference position SOD) shifted by a slice thickness d are set as tomographic planes FP of the subject T. The slice thickness d is a distance between tomographic planes FP, and each tomographic plane FP is arranged at equal intervals in the Z-direction with the slice thickness d. "j" denotes a tomographic position number. "+j" pieces of tomographic images FP are set on the positive side (detector 2 side) with respect to the reference position SOD. "−j" pieces of tomographic images 40 are set on the negative side (X-ray source 1 side) with respect to the reference position SOD. Assuming that the coordinate of the SOD in the Z-direction is z, the tomographic position of each tomographic plane FP is expressed as (z−jd)−(z+jd).

The position information acquisition unit 171 acquires the slice thickness d and the tomographic position number (j) of the tomographic plane FP as the tomographic position (z±j d) of the imaging target tomographic plane FP in the Z-direction. Note that the position information acquisition unit 171 acquires the reference position SOD as known information.

Then, the image processing unit 160 is configured to acquire the phase distribution in the tomographic plane FP, based on the deviation (±jd) of the tomographic position with respect to the reference position SOD (=z) and the reference position SOD in the Z-direction and the relative position of the imaging system 9 and the subject T in a predetermined direction (X-direction).

As shown in FIG. 20, the subject T is moved to the respective relative positions by the moving mechanism 5 and is imaged. The position of the subject T in the coordinate system on the moving mechanism 5 is expressed as $x(x_0$ to $x_i)$. i is the number for identifying the relative position. For example, the first imaging position to the sixth imaging position in FIG. 8 are $x_1$ to $x_6$ when $x_0$ is the initial position. The X-coordinate of the projected point of the point belonging to each tomographic plane FP (0 to +j) to the detection surface (image 10) in each position coordinate $x_0$ to $x_i$ is defined as $x_d$ ($x_{d00}$ to $x_{dji}$). Note that the same applies to the respective tomographic planes FP (0 to −j). Further, the region from $X_{d00}$ to $X_c$ is a region in which X-rays that have passed through the first grating region R1 are detected. Further, the region from $X_c$ to $X_{d0i}$ is a region in which the X-rays that have passed through the second grating region R2 are detected.

When the points B1 to B3 of the subject T are moved to the position $x_0$, the X-rays passing through the point B1 (tomographic position number=0) shift to the coordinate of $x_{d00}$ of the detection surface (image 10). On the other hand, the X-rays passing through the point B2 (tomographic position number=1) shifts to the coordinate of $x_{d10}$ of the detection surface (image 10), and the X-rays passing through the point B3 (tomographic position number=j) shifts to the coordinate of $x_{dj0}$ of the detection surface (image 10). When the position coordinate $x_i$ of the subject T and the tomographic position (tomographic position number j) are determined, the position coordinate $x_{dji}$ of the detection surface (image 10) is specified. For this reason, the relative position between the imaging system 9 and the subject T is represented by $x_i$ in the coordinate system of the moving mechanism 5 and represented by $x_{dji}$ in the coordinate system of the image 10.

Figure 21:
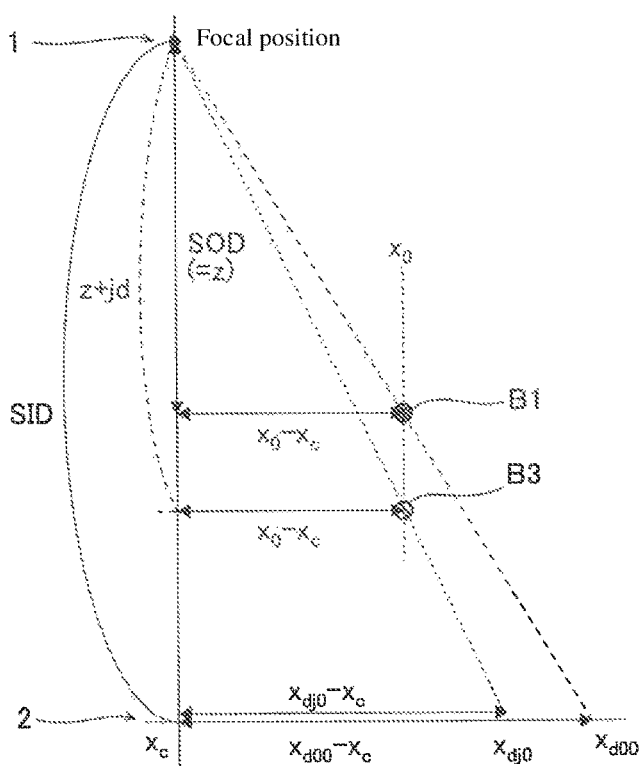
FIG. 21 is a schematic diagram showing the geometrical relation between the X-ray source, the point on the tomographic plane in the subject, and the detector.

In FIG. 20, the point B1 of the tomographic position number j=0 at the position $x_0$ of the subject T and the position coordinate $x_{d00}$ on the detection surface (image 10) are represented by the following relational expression (Expression (6)) from the correlation shown in FIG. 21. $x_c$ represents the X-coordinate of the optical axis XRa (normal line passing through the focal point) on the detection surface (image 10).

$$x_{d00} - x_c = (x_0 - x_c)\frac{SID}{SOD} = (x_0 - x_c)\frac{SID}{z} \quad (6)$$

Here, at the position $x_0$ of the subject T, for the point (point B3) at the $j^{th}$ tomographic position z+jd from the reference position SOD, the X-coordinate $x_{dj0}$ reflected on the detection surface (image 10) is represented by the following relational expression (Expression (7)) from the correlation shown in FIG. 21.

$$x_{dj0} - x_c = (x_0 - x_c)\frac{SID}{z + jd} = \frac{z}{z + jd}(x_{d00} - x_c) \quad (7)$$

As can be understood from Expression (7), it is possible to transform from the position coordinate $x_{d00}$ on the reference position SOD (=z) to the position coordinate $x_{dj0}$ on any tomographic plane FP. The position coordinate $x_{d00}$ and the position coordinate $x_{dj0}$ are represented by a relation that does not depend on the SID.

Therefore, the position coordinate $x_{dji}$ of the point of any $j^{th}$ tomographic position when the subject T is moved to any $i^{th}$ position $x_i$ by the moving mechanism 5 is represented by the following Expression (8).

$$x_{dji} - x_c = \frac{z}{z + jd}(x_{d0i} - x_c) \quad (8)$$

By arranging the above-described Expression (8), the following Expression (9) is acquired.

$$x_{dji} = \frac{z}{z + jd}x_{d0i} + \left(1 - \frac{z}{z + jd}\right)x_c \quad (9)$$

From the above, the position coordinate of each image 10 in which the subject T is imaged at each relative position $x_i$ in a predetermined direction (X-direction) by the moving mechanism 5 can be converted to the position coordinate of the tomographic image on the tomographic plane FP at any tomographic position (z+j d) deviating from the reference position SOD.

As described above, the image processing unit 160 is configured to acquire the phase distribution on the tomographic plane FP, based on the deviation (jd) of the tomographic position with respect to the reference position SOD (=z) and the tomographic position in the Z-direction and the relative position ($x_{d0i}$) of the imaging system 9 and the subject T in the predetermined direction (X-direction).

Note that the relative position ($x_{d0i}$) of the subject T is acquired by the following Expression (10).

$$x_{d0i} = x_{start} + p1 \times np \quad (10)$$

Here, $X_{start}$ is the initial position of the subject T at the imaging initiation time. Further, p1 is the transformation coefficient [pixel/pulse] of the movement amount of the actual subject T in the image 10 with respect to the command value (the number of pulses) input to the moving mechanism 5. np is a command value (the number of pulses) input to the moving mechanism 5 when moving the subject T to each relative position of $x_0$ to $x_i$.

For each of the acquired images 10, the image processing unit 160 acquires each relative position ($x_{d0i}$) of the subject T by the above-described Expression (10) and substitutes it to the above-described Expression (9), thereby performing the coordinate transformation so as to become the tomographic image of the tomographic plane FP specified by the tomographic position number j.

(Generation of Position Calibration Data)

In the above-described Expression (10), the transformation coefficient p1 [pixel/pulse] is a part of the design specification of the moving mechanism 5 and can be acquired in advance as known information. In contrast, in the third embodiment, the image processing unit 160 is configured to generate the position calibration data associating the movement amount dm of the moving mechanism 5 with the amount of change of the relative position ($x_{d0i}$) in the image 1 and acquire the phase distribution in the tomographic plane FP using the position calibration data acquired at the reference position SOD. The configuration in which the image processing unit 160 acquires the position calibration data is the same as the configuration in which the image processing unit 6 (60) acquires the position calibration data in the first and second embodiments, and therefore the detailed descriptions thereof are omitted.

Figure 22:
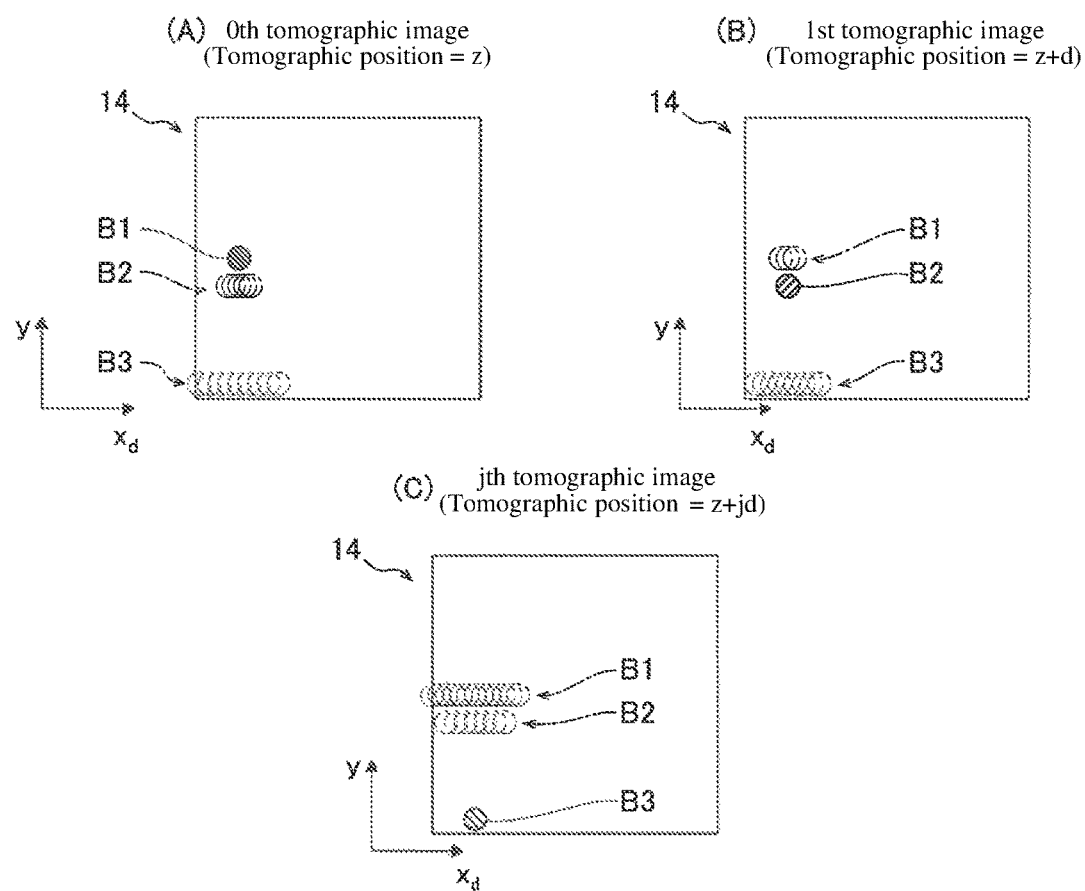
FIG. 22 shows schematic diagrams (A) to (C) for explaining how a subject is reflected in the tomographic image at each tomographic position.

The phase-contrast image 14 (first phase-contrast image 14*a* and second phase-contrast image 14*b*) to be generated becomes a tomographic image at the tomographic position (z+jd) acquired by the position information acquisition unit 171. FIG. 22 is a conceptual diagram of the tomographic image (phase-contrast tomographic image) of the phase-contrast image 14.

As shown in (A) of FIG. 22, for example, when the reference position SOD (=z) is acquired as a tomographic position, the respective images 10 and phase information 12 are converted to the stationary coordinate system of the subject T based on the point B1 on the tomographic plane FP at the tomographic position (=z), so that the tomographic image (absorption image 15, phase differential image 16, dark-field image 17) focused on the tomographic plane at the tomographic position=z is generated. At this time, in the image at the point B2 and the image at the point B3 in the different tomographic planes FP, blurring occurs.

As shown in (B) of FIG. 22, when the tomographic position (z+d) in the tomographic plane FP having the point B2 is acquired, by converting to the stationary coordinate system of the subject T based on the point B2 on the tomographic plane FP at the tomographic position=z+d, a tomographic image focused on the tomographic plane FP at the tomographic position=z+d is generated. At this time, in the image at the point B1 and the image at the point B3 in the different tomographic planes FP, blurring occurs.

As shown in (C) of FIG. 22, when the tomographic position (z+jd) in the tomographic plane FP having the point B3 is acquired, by converting to the stationary coordinate system of the subject T based on the point B3 in the tomographic plane FP at the tomographic position=z+jd, a tomographic focused on the tomographic plane FP at the tomographic position=z+jd is generated. At this time, in the image at the point B1 and the image at the point B2 in different tomographic planes FP, blurring occurs.

As described above, in the third embodiment, a phase-contrast tomographic image in which blurring is suppressed (image is focused) at any tomographic plane FP specified by the user can be obtained.

In the third embodiment, the image processing unit 160 is configured to individually generate a tomographic image based on the plurality of images 10 captured in the first grating region R1 and the second grating region R2. That is, the image processing unit 160 is configured to individually generate the first phase-contrast image 14*a* at a predetermined tomographic plane FP and the second phase-contrast image 14*b* at a predetermined tomographic plane FP. The image processing unit 160 may be configured to generate an image in which the first phase-contrast image 14*a* in the predetermined tomographic plane FP and the second phase-contrast image 14*b* in a predetermined tomographic plane FP.

Figure 23:
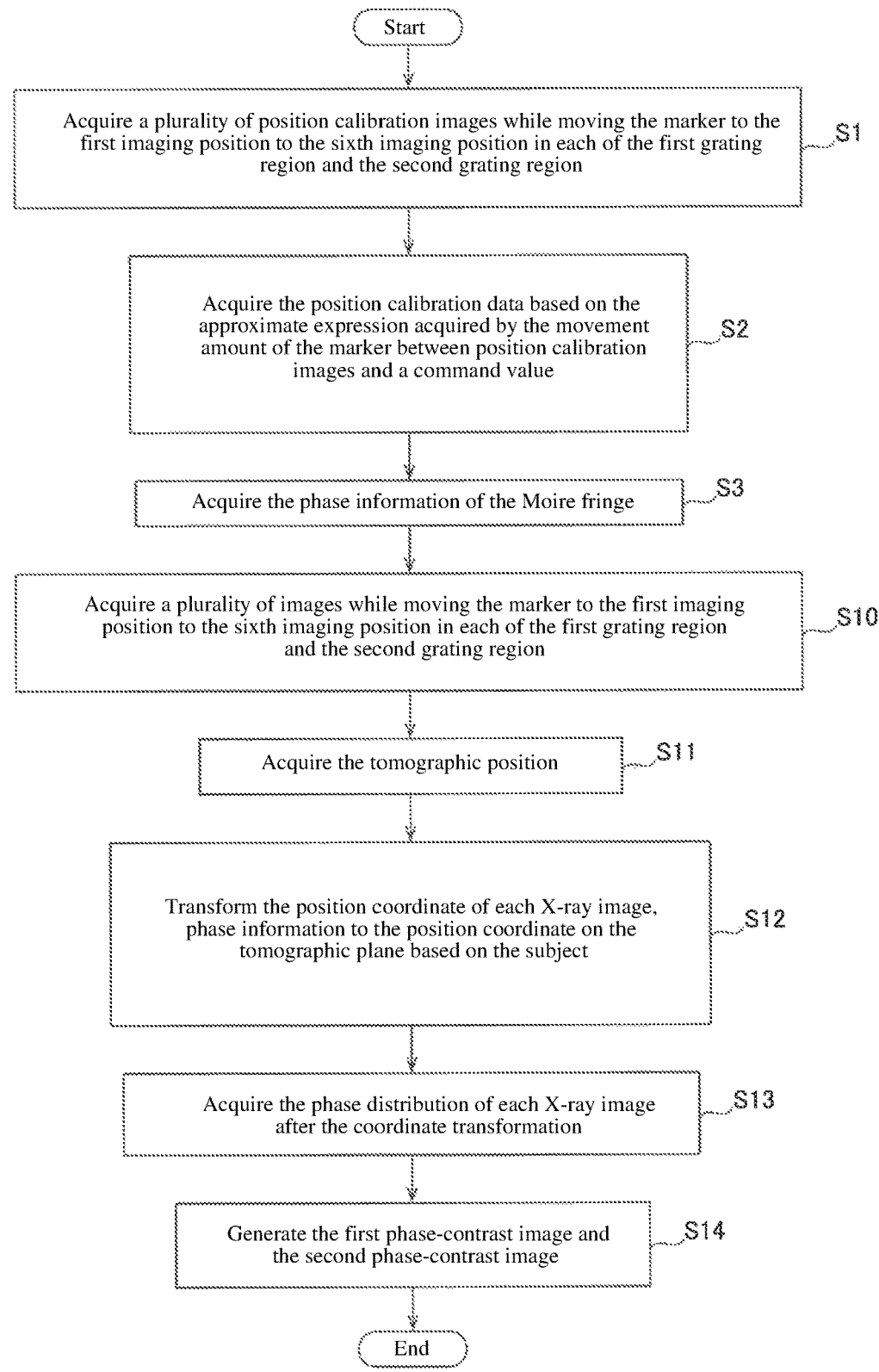
FIG. 23 is a flowchart for explaining the generation processing of the phase-contrast image by the X-ray phase imaging system according to the third embodiment.

Next, referring to FIG. 23, the flow of processing for generating the phase-contrast image 14 (first phase-contrast image 14*a* and second phase-contrast image 14*b*) by the X-ray phase imaging system 300 according to the third embodiment will be described. It should be noted that the detailed descriptions of the step for performing the same processing as that of the first and second embodiments will be omitted.

In Steps S1 to S3 and Step S10, the image processing unit 160 generates a plurality of position calibration images 13 at the respective relative positions. In addition, the image processing unit 160 acquires an approximate expression (position calibration data) based on the movement amount dm of the marker M and the command value. Further, the image processing unit 160 acquires the phase information 12 of the Moire fringe MF. Further, the image processing unit 160 acquires a plurality of images 10 at a plurality of relative positions in the X-direction by the moving mechanism 5. The moving mechanism 5 moves the subject T to each relative position of $x_0$ to $x_i$.

Next, in Step S11, the position information acquisition unit 171 acquires the tomographic position. The position information acquisition unit 171 acquires each set value of the SOD (=z), the slice thickness d, and the tomographic position number j, which are set by a user, for example. The acquisition processing of the tomographic position (z+jd) may be performed at any time prior to Step S12.

Next, in Step S12, the image processing unit 160 performs the coordinate transformation of the position coordinate of each of the images 10 and phase information 12 acquired at each relative position based on the point on the tomographic plane FP specified by the acquired tomographic position (z+jd) in the subject T. With this, the image processing unit 160 acquires each of the coordinate transformed subject images 21 (see FIG. 9) and phase information 22 (see FIG. 9) coordinate transformed to the stationary coordinate system based on the subject T on the tomographic plane FP.

Next, in Step S13, the image processing unit 160 acquires the phase distribution in the tomographic plane FP based on each subject image 21 and each phase information 22 after the coordinate transformation. That is, the image processing unit 160 generates the intensity signal curve SC2 (see FIG. 17) of the respective pixels (respective position coordinates) in a stationary coordinate system based on the subject T on the tomographic plane FP.

In Step S14, the image processing unit 160 generates the phase-contrast image 14 (first phase-contrast image 14*a* and second phase-contrast image 14*b*) at a predetermined tomographic plane FP based on the generated intensity signal curve SC2. Note that the image processing unit 160 may generate the absorption image 15, the phase differential image 16, and the dark-field image 17 as the phase-contrast image 14. Thus, the generation processing of the phase-contrast image 14 is completed.

Note that in the same manner as in the first and second embodiments, either the processing of Step S1 and Step S2 or the processing of Step S3 may be performed first. Further, the acquisition processing of the position calibration data may be performed at any time as long as it is prior to the coordinate transformation of a plurality of images 10. Further, the processing of acquiring the phase information 12 of the Moire fringe MF may be performed at any time as long as it is prior to the coordinate transformation of the phase information 12.

The rest of the configuration of the third embodiment is the same as that of the first and second embodiments.

(Effects of Third Embodiment)

In the third embodiment, the following effects can be obtained.

In the third embodiment, as described above, it is further provided with the position information acquisition unit 171 for acquiring the tomographic position on the imaging target tomographic plane FP in the Z-direction. The image processing unit 160 is configured to generate the first phase-contrast image 14a and the second phase-contrast image 14b in the tomographic plane FP by acquiring the plurality of images 10 of the subject T captured at a plurality of relative positions of the imaging system 9 and the subject T in a predetermined direction and the phase distribution in the tomographic plane FP based on the acquired tomographic position. With this, among the subject T, the position (tomographic position) in the tomographic plane FP in the Z-direction in which the internal structure to be imaged exists can be acquired by the position information acquisition unit 171. Since the incident angle of the X-rays with respect to the point on the tomographic plane FP is determined by the relative position between the imaging system 9 and the subject T, the position of the point on the tomographic plane FP in each image 10 can be identified by the information of the tomographic position and the relative position when the image 10 is captured. This allows the image processing unit 160 to acquire the phase distribution at a particular tomographic plane FP indicated by the tomographic position, based on the information of the acquired tomographic position and the respective images 10 at the plurality of relative positions. Consequently, from the phase distribution in the tomographic plane FP at the tomographic position acquired by the position information acquisition unit 171, the phase-contrast image 14 (tomographic image) in which blurring of images is suppressed for the internal structure included in the tomographic plane FP is acquired. With this, even if the subject T has a large thickness, it is possible to suppress the deterioration of the visibility of the internal structure.

The other effects of the third embodiment are the same as those of the above-described first and second embodiments.

Fourth Embodiment

Next, referring to FIG. 24 and FIG. 25, an X-ray phase imaging system 400 according to a fourth embodiment (see FIG. 24) will be described. Unlike the above-described first and second embodiments in which the phase-contrast image 14 is generated based on the images 10 captured while passing the subject T through the first grating region R1 and the second grating region R2, in the fourth embodiment, the moving mechanism 5 is configured to relatively move the subject T and the imaging system 9 such that the subject T passes through no grating region R3 in which the first grating group 3 and the second grating group 4 are not arranged. Note that the same configuration as that of the first and second embodiments is denoted by the same reference symbol, and the descriptions thereof will be omitted.

(Configuration of X-Ray Phase Imaging System)

First, referring to FIG. 24, the configuration of the X-ray phase imaging system 400 according to the fourth embodiment will be described.

In the fourth embodiment, the X-ray phase imaging system 400 has the same configuration as the above-described first embodiment except that it is provided with a collimator 50 and an image processing unit 260. The moving mechanism 5 is configured to relatively move the subject T and the imaging system 9 such that the subject T passes through no grating region R3 in which the first grating group 3 and the second grating group 4 are not arranged. The image processing unit 260 is configured to display the second composite image 23 in which the first phase-contrast image 14a (first phase differential image 16a) and the second phase-contrast image 14b (second phase differential image 16b), and the absorption image 150 (see FIG. 25) acquired when the subject T has passed through no grating region R3.

The collimator 50 is arranged between the first grating 30 and the first grating 40 and the second grating 31 and the second grating 41. The collimator 50 is constituted by a shielding member for shielding X-rays and is formed with collimator holes 50a and 17b which are configured to be freely opened and closed. The collimator hole 50a can adjust the irradiation range of the X-rays emitted to the detector 2 through the first grating group 3 and the second grating group 4, among the X-rays emitted from the X-ray source 1. The collimator hole 50b can adjust the range of the X-rays emitted to the detector 2 without passing through the first grating group 3 and the second grating group 4. The size of the first grating region R1 and the second grating region R2 in the X-direction is adjusted to a size in which at least one period d7 of the Moire fringe MF (see FIG. 4) is reflected. Since the no grating region R3 is a region for capturing the absorption image 150 (see (A) of FIG. 25) in which no grating is intervened, the size of the no grating region R3 in the X-direction may be smaller than the size of one period d7 of the Moire fringe MF.

Figure 24:
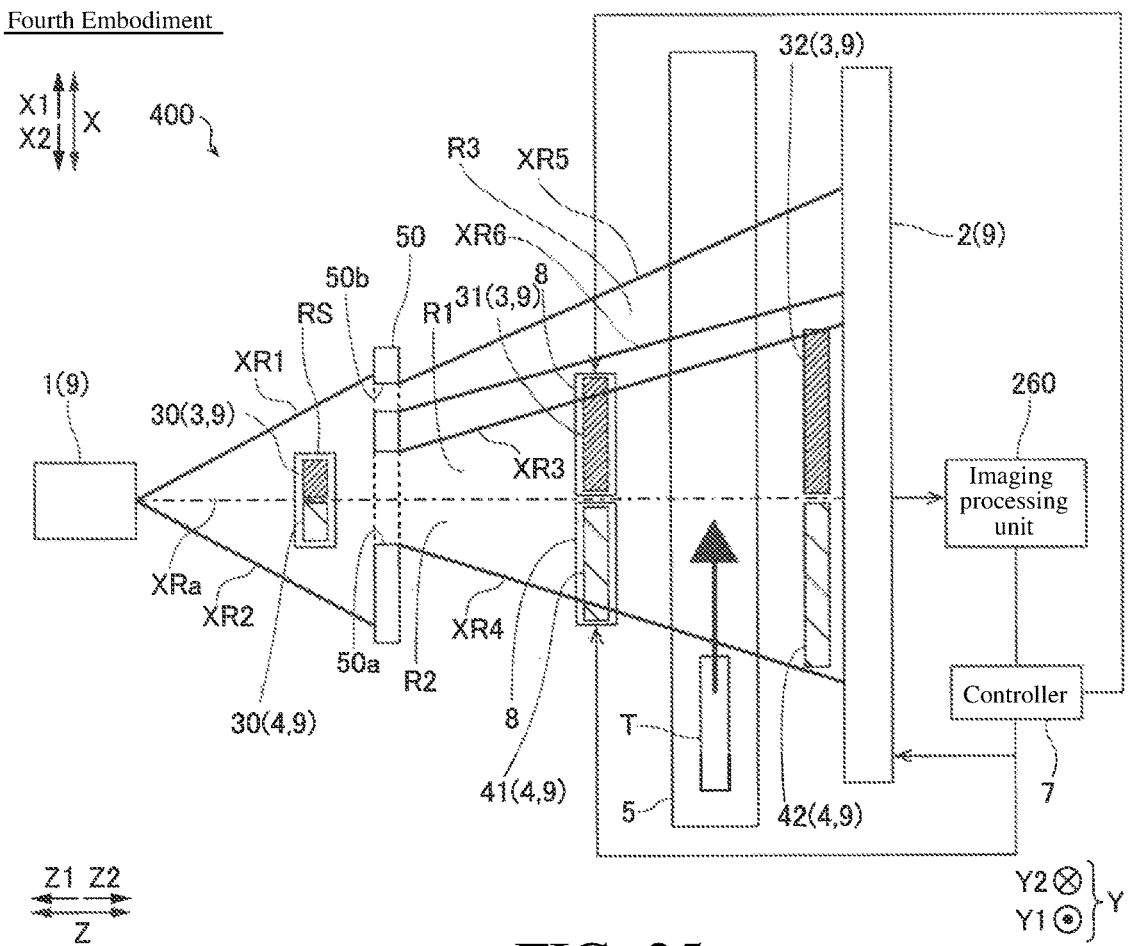
FIG. 24 is a schematic diagram showing the entire configuration of the X-ray phase imaging system according to the fourth embodiment.

In the example shown in FIG. 24, the first grating region R1 is a region formed by the optical axis XRa of the X-rays, the straight line XR1 showing the irradiation range of the X-rays from the X-ray source 1 to the collimator 50, and the straight line XR3 showing the irradiation range of the X-rays from the collimator 50 to the detector 2. Further, in the example shown in FIG. 24, the second grating region R2 is a region formed by the optical axis XRa of the X-rays, the straight line XR2 showing the irradiation range of the X-rays from the X-ray source 1 to the collimator 50, and the straight line XR4 showing the irradiation range of the X-rays from the collimator 50 to the detector 2. In the case shown in FIG. 24, the no grating region R3 is a region formed by the straight line XR4 and the straight line XR5 indicating the irradiation range of X-rays from the collimator 50 to the detector 2.

Figure 25:
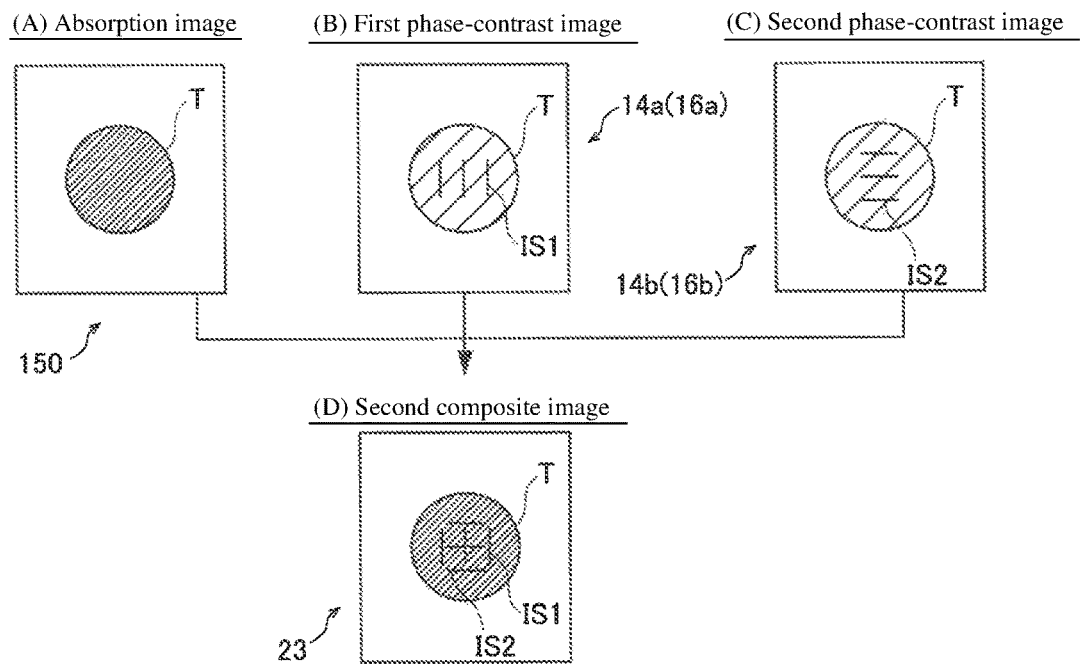
FIG. 25 is a schematic diagram of the absorption image (A), the first phase-contrast image (B), the second phase-contrast image (C), and the second composite image (D) acquired by composing them, which are generated by an image processing unit according to a fourth embodiment.

As shown in FIG. 25, in the fourth embodiment, the image processing unit 260 is configured to display the second composite image 23 in which the first phase-contrast image 14a and the second phase-contrast image 14b are composed with the absorption image 150. In the example shown in (B) of FIG. 25, as the internal structure of the subject T, a first phase-contrast image 14a in which the internal structure IS1 extending in the Y-direction is depicted. Further, in (C) of FIG. 25, as the internal structure of the subject T, the second phase-contrast image 14b in which the internal structure IS2 extending in the X-direction is depicted is illustrated. The X-ray absorptions of the internal structure IS1 and the internal structure IS2 are of such a magnitude that they are not depicted in the absorption image 150.

The second composite image 23 is generated by composing the absorption image 150, the first phase-contrast image 14a (first phase differential image 16a), and the second phase-contrast image 14b (second phase differential image 16b). Therefore, the sensitivity of the internal structure IS1 in the Y-direction and the sensitivity of the internal structure IS2 in the X-direction can be grasped in one second composite image 23.

Figure 26:
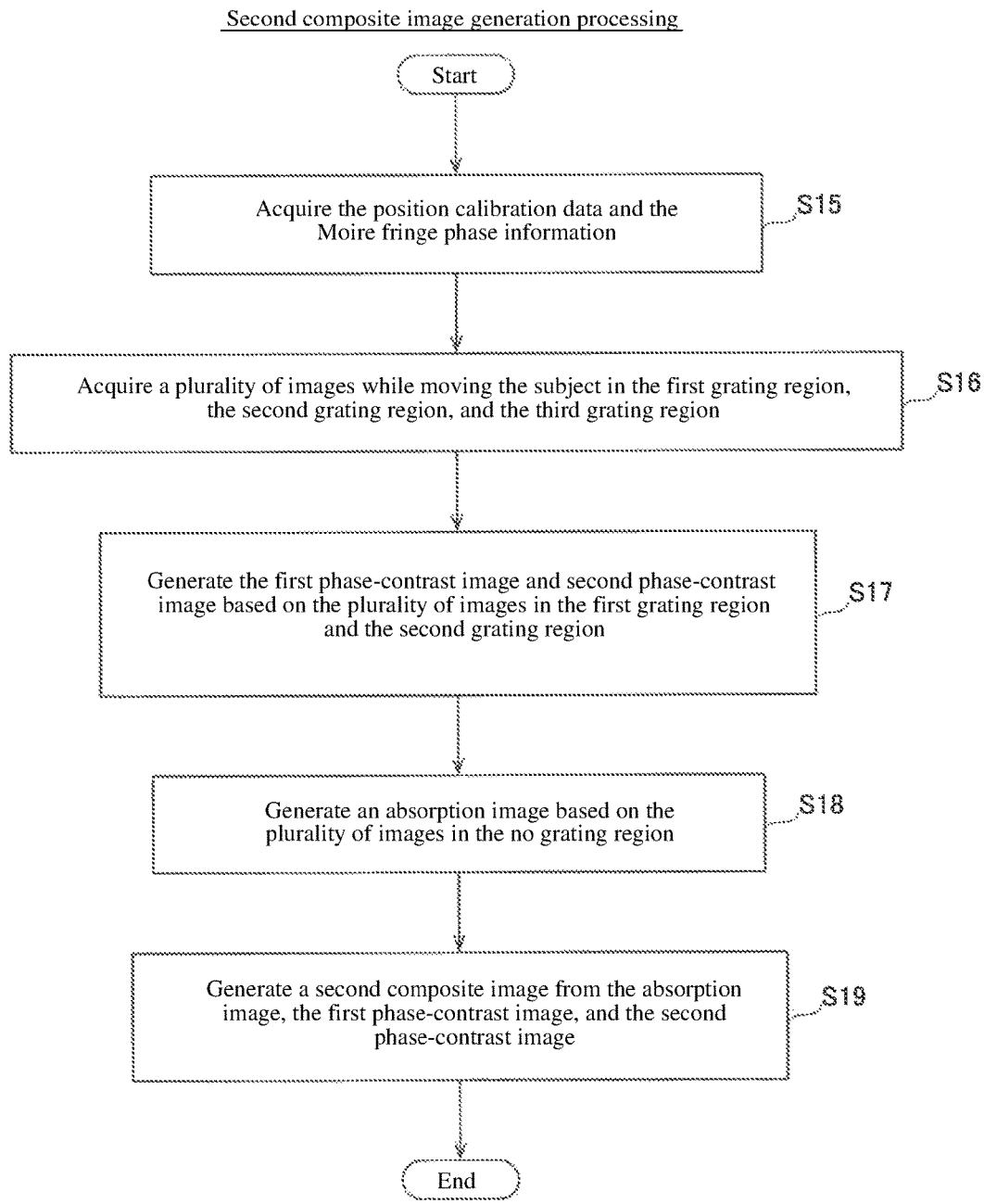
FIG. 26 is a flowchart for explaining the generation processing of the second composite image by the X-ray phase imaging system according to the fourth embodiment.

Next, referring to FIG. 26, the flow of processing for generating the second composite image 23 in the X-ray phase imaging system 400 by the fourth embodiment will be described.

In Step S15, the controller 7 acquires the position calibration data and the phase information 12 of the Moire fringe MF. Since the acquisition processing of the position calibration data and the phase information 12 of the Moire fringe MF in Step S15 is the same as the processing of Step S1 to Step S3 in the first embodiment, the detailed descriptions thereof are omitted. Thereafter, the processing proceeds to Step S16.

In Step S16, the image processing unit 260 acquires a plurality of images 10 captured while moving the subject T in the first grating region R1, the second grating region R2, and the no grating region R3. Thereafter, in Step S17, the image processing unit 260 generates the first phase-contrast image 14a (first phase differential image 16a) and the second phase-contrast image 14b (second phase differential image 16b), based on the plurality of images 10 in the first grating region R1 and the second grating region R2. Thereafter, the processing proceeds to Step S18.

In Step S18, the image processing unit 260 generates the absorption image 150 based on the images 10 in the no grating region R3. Thereafter, in Step S19, the image processing unit 260 generates the second composite image 23 in which the first phase-contrast image 14a (first phase differential image 16a) and the second phase-contrast image 14b (second phase differential image 16b), and the absorption image 150 are composed, and ends the processing.

It should be noted that either the processing of Step S17 or the processing of Step S18 may be performed first.

The rest of the configuration of the fourth embodiment is the same as that of the first and secondary embodiments.

(Effects of Fourth Embodiment)

In this fourth embodiment, the following effects can be obtained.

In the fourth embodiment, as described above, the moving mechanism 5 is configured to relatively move the subject T and the imaging system 9 such that the subject T passes through the no grating region R3 in which the first grating group 3 and the second grating group 4 are not arranged. The image processing unit 260 is configured to display the second composite image 23 in which the first phase-contrast image 14a (first phase differential image 16a) and the second phase-contrast image 14b (second phase differential image 16b), and the absorption image 150 acquired when the subject has passed through the no grating region R3 are composed. With this, without performing imaging with the first grating group and the second grating group retracted, or performing imaging using another imaging apparatus not including a grating, it is possible to generate the absorption image 150 captured without intervening a grating, the first phase-contrast image 14a (first phase differential image 16a), and the second phase-contrast image 14b (second phase differential image 16b) captured using a grating can be generated. Since the X-rays reaching the no grating region R3 reach the detector 2 without passing through a grating, it is possible to suppress the attenuation of the X-rays due to gratings, in particular, the attenuation of the X-rays due to the low-energy sides. As a result, as compared with the absorption image 15 (see (A) of FIG. 12) generated by the X-rays that have passed through the first grating region R1 and the second grating region R2, it is possible to improve the contrast of the absorption image 150 generated by the X-rays that have passed through the no grating region R3.

Note that the other effects of the fourth embodiment are the same as those of the above-described first and second embodiments.

(Modifications)

It should be understood that the embodiments disclosed here are examples in all respects and are not restrictive. The scope of the present invention is indicated by the appended claims rather than by the descriptions of the above-described embodiments and includes all modifications (changes) within the meanings and the scopes equivalent to the scope of the claims.

Figure 27:
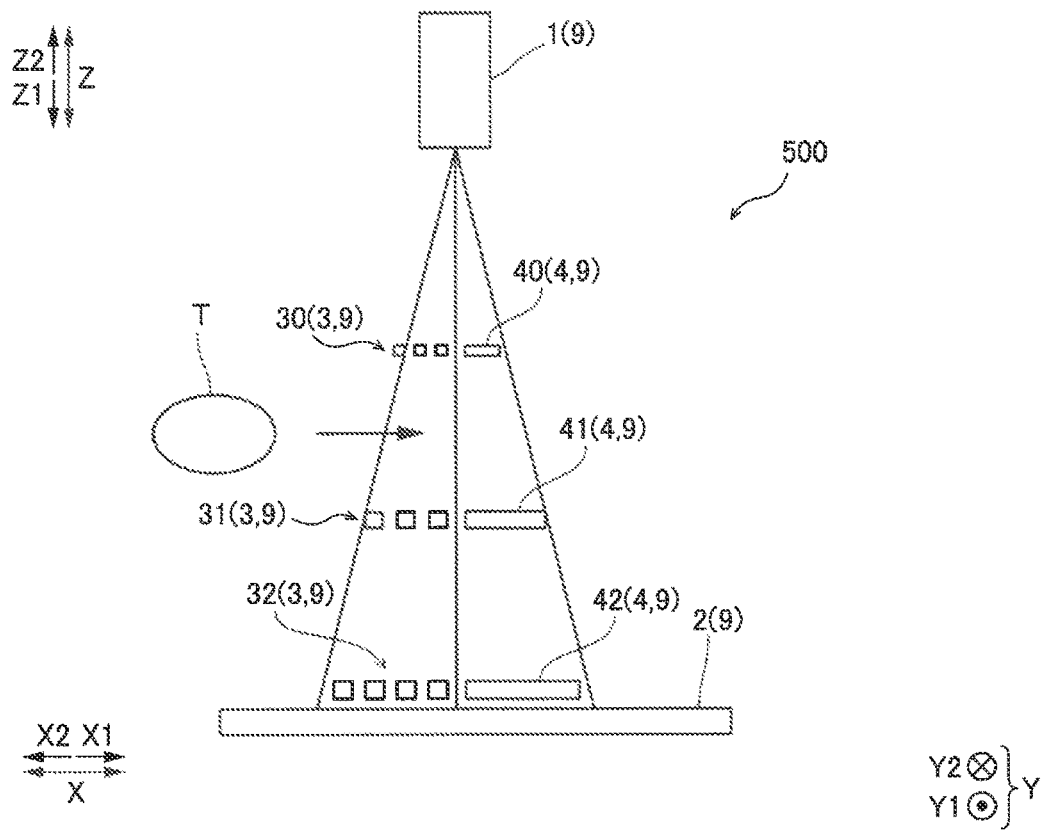
FIG. 27 is a schematic diagram showing the entire configuration of the X-ray phase imaging system according to a first modification.

For example, in the above-described first, second, and fourth embodiments, although an example is shown in which it is configured such that the Z-direction is the horizontal direction and the imaging system 9 is arranged along the horizontal direction, but the present invention is not limited thereto. For example, as in the X-ray phase imaging system 500 shown in FIG. 27, the Z-direction may be the vertical direction, and the imaging system 9 may be arranged along the vertical direction.

Figure 28:
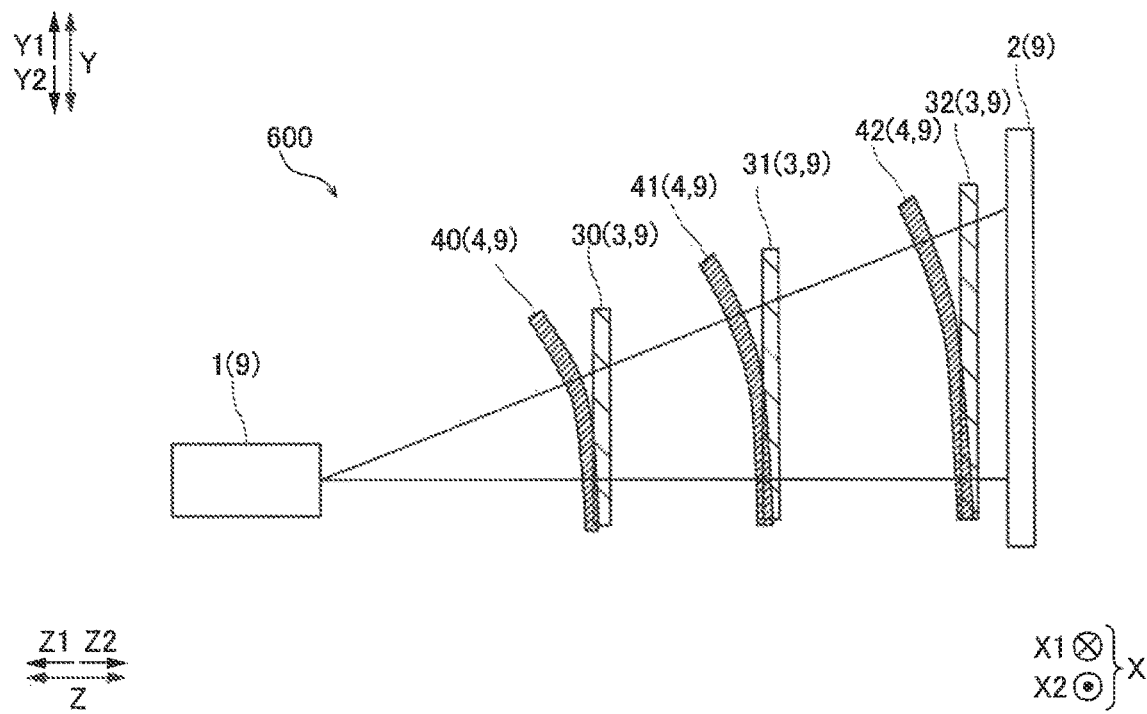
FIG. 28 is a schematic diagram showing the entire configuration of the X-ray phase imaging system according to the second modification.

In addition, in the above-described first to fourth embodiment, an example is shown in which it is configured such that each grating is in a flat plate shape, but the present invention is not limited thereto. For example, in a case where the subject T to be imaged is large, the range of the X-rays to be emitted also increases. Thus, it is necessary to use a grating having a large area. When the irradiation range of X-rays increases, in some cases, the X-rays are incident on the grating from the oblique direction. In this case, since the X-rays are incident from the oblique direction even for each slit and each X-ray transmission portion, unintentional absorption occurs in each X-ray absorption portion, etc. Therefore, the dose of the X-rays reaching the detector 2 is reduced, resulting in the decreased contrast of the phase-contrast image 14. Therefore, as in the X-ray phase imaging system 600 shown in FIG. 28, the grating may be curved. In the example shown in FIG. 28, an example is shown in which the grating of the second grating group 4 is curved. Depending on the size of the grating, only the first grating 40 may be curved. Further, each grating of the first grating group 3 may be curved. Further, the grating of the first grating group 3 may be curved.

Further, in the first to fourth embodiments described above, an example is shown in which it is configured such that the X-ray phase imaging system 100 (200, 300, 400) is provided with the first grating 30 and the first grating 40, but the present invention is not limited thereto. In a case where the coherence of the X-rays emitted from the X-ray source 1 is sufficiently high such that it is possible to form a self-image of the second grating 31 and the second grating 41, the first grating 30 and the first grating 40 may not be provided.

Further, in the first to fourth embodiments described above, an example is shown in which the grating moving mechanism 8 moves the second grating 31 and the second grating 41 when acquiring the phase information 12, but the present invention is not limited thereto. The grating to be moved may be any grating.

Further, in the second embodiment described above, an example is shown in which it is configured such that imaging is performed while moving the subject T (marker M) to six positions of the first imaging position to the sixth imaging position, the present invention is not limited thereto. As long as it is possible to acquire the intensity signal curve SC2, the number of positions for arranging the subject T (marker M) may be less than 6 or more than 6.

In the above-described second embodiment, an example is shown in which it is configured such that the subject T is moved by the same movement amount dt as the movement amount dm of the marker M, but the present invention is not limited thereto. The movement amount dt of the subject T and the movement amount dm of the marker M may not be the same.

Further, in the first to fourth embodiments described above, an example is shown in which it is configured such that the subject T (marker M) is moved between the second grating 31 and the second grating 41, and the third grating 32 and the third grating 42, but the present invention is not limited thereto. For example, it may be configured to move the subject T (marker M) between the first grating 30 and the first grating 40 and the second grating 31 and the second grating 41.

Further, in the above-described first to fourth embodiments, an example is shown in which it is configured such that the position calibration data is generated by acquiring the approximate expression based on the command value and the movement amount dm, but the present invention is not limited thereto. As long as it is possible to acquire the position of the pixel in each image 10, the position calibration data may be generated in any way.

Further, in the first and second embodiments, an example is shown in which it is configured such that the image processing unit 6 (60) generates the first composite image 19 from the first phase differential image 16a and the second phase differential image 16b, but the present invention is not limited thereto. For example, the image processing unit 6 (60) may be configured to generate the first composite image 19 using the dark-field image 17 captured at the first grating region R1 and the dark-field image 17 captured at the second grating region R2. Further, the image processing unit 6(60) may be configured to generate the first composite image 19 by composing the first phase differential image 16a and the second phase differential image 16b with the dark-field image 17 captured in the first grating region R1 and the dark-field image 17 captured in the second grating region R2.

Further, in the first and second embodiments, an example is shown in which it is configured such that the image processing unit 6 (60) generates the first composite image 19 from the first phase differential image 16a and the second phase differential image 16b, but the present invention is not limited thereto. For example, the image processing unit 6 (60) may only generate the first phase differential image 16a (first phase-contrast image 14a) and the second phase differential image 16b (second phase-contrast image 14b), without generating the first composite image 19.

Further, in the above-described fourth embodiment, an example is shown in which it is configured such that the image processing unit 160 generates the second composite image 23 in which the absorption image 150, the first phase-contrast image 14a, and the second phase-contrast image 14b are composed, but the present invention is not limited thereto. For example, the image processing unit 160 may be configured to display the absorption image 150, and the first phase-contrast image 14a, and the second phase-contrast image 14b side by side by outputting the absorption image 150, and the first phase-contrast image 14a, and the second phase-contrast image 14b to an external display device or the like.

Further, in the above-described first to fourth embodiments, an example is shown in which it is configured such that the acquisition of the position calibration data and the phase information 12 of the Moire fringe MF and the imaging of the subject T are performed successively, but the present invention is not limited thereto. The processing of acquiring the position calibration data and the phase information 12 of the Moire fringe MF may be performed in advance and stored in a storage unit or the like. In a case where the position calibration data and the phase information 12 of the Moire fringe MF are stored in a storage unit or the like, the image processing unit 6 (60, 160, 260) may be configured to acquire the position calibration data and the phase information 12 of the Moire fringe MF from the storage unit when generating the phase-contrast image 14.

Further, in the above-described first to fourth embodiments, an example is shown in which it is configured such that the moving mechanism 5 moves the subject T (marker M) from the X2-direction to the X1-direction, but the present invention is not limited thereto. For example, the moving mechanism 5 may be configured to move the subject T (marker M) from the X1-direction to the X2-direction. As long as it is possible to move the subject T (marker M) in the periodic direction of the Moire fringe MF, the moving mechanism 5 may move the subject T (marker M) in any way.

Further, in the above-described first to fourth embodiments, an example is shown in which it is configured such that the imaging is performed in a state in which the imaging system 9 is fixed and the moving mechanism 5 moves the subject T, but the present invention is not limited thereto. For example, the moving mechanism 5 may be configured to relatively move the subject T and the imaging system 9 by moving the imaging system 9 with the subject T fixed. Further, it may be configured to acquire the position calibration data by moving the imaging system 9 with the marker M fixed. Since it is enough that the relative position of the subject T (marker M) and the imaging system 9 changes, the moving mechanism 5 may move either one of the subject T (marker M) and the imaging system 9. Note that in the first to third embodiments, in a case where the moving mechanism 5 moves the imaging system 9, the moving mechanism 5 may be configured to move the grating moving mechanism 8 together with the grating. Further, in the fourth embodiment, in a case where the moving mechanism 5 moves the imaging system 9, the moving mechanism 5 may be configured to move the collimator 50 together with the imaging system 9.

In addition, in the above-described first and second embodiments, an example is shown in which it is configured such that the image processing unit 6 (60) generates the first composite image 19 by the above-described Expression (4), but the present invention is not limited thereto. The image processing unit 6 (60) may be configured to generate the first composite image 19 without using the above-described Expression (4). For example, the image processing unit 6(60) may be configured to generate the first composite image 19 by simply adding the first phase-contrast image 14a and the second phase-contrast image 14b. Further, the image processing unit 6 (60) may be configured to generate the first composite image 19 by acquiring the square root of sum of squares of the first phase-contrast image 14a of the square root of sum of squares of the second phase-contrast image 14b.

Further, in the above-described fourth embodiment, an example is shown in which it is configured such that the first grating group 3, the second grating group 4, and collimator 50 are arranged such that the respective regions are arranged in the order of the second grating region R2, the first grating region R1, and the no grating region R3 in the direction from the X2-direction toward the X1-direction, but the present invention is not limited thereto. The order of the first grating region R1, the second grating region R2, and the no grating region R3 may be any order. Note that in the X-direction, in a case where the first grating group 3 is placed at a position away from the optical axis XRa, since it is required to arrange the first grating group 3 at an angle depending on the irradiation direction of the X-rays, the first grating group 3 is preferably arranged at a position (front side of the X-ray source 1) near the optical axis XRa.

DESCRIPTION OF SYMBOLS

1: X-ray source
2: Detector
3: First grating group
4: Second grating group
5: Moving mechanism
6, 60, 160, 260: Image processing unit
7, 70, 170: Controller
8: Grating moving mechanism
9: Imaging system
10, 21: Image (multiple images captured while relatively moving the subject and the imaging system)
12, 22: Phase information
13: Position calibration image
14: Phase-contrast image
14a: First phase-contrast image
14b: Second phase-contrast image
15: Absorption image (phase-contrast image)
16: Phase differential image (phase-contrast image)
17: Dark-field image (phase-contrast image)
18: Phase image
19: First composite image
23: Second composite image
30: First grating (first grating group)
31: Second grating (first grating group)
32: Third grating (first grating group)
40: First grating (second grating group)
41: Second grating (second grating group)
42: Third grating (second grating group)
71: Position information acquisition unit
100, 200, 300, 400, 500, 600: X-ray phase imaging system
FP: Imaging target tomographic plane
M: Marker
MF: Moire fringe
R1: First grating region
R2: Second grating region
R3: No grating region
T: Subject

The invention claimed is:

1. An X-ray phase imaging system comprising:
an X-ray source;
a detector configured to detect X-rays emitted from the X-ray source;
a first grating group including a plurality of gratings arranged along an optical axis direction of the X-rays between the X-ray source and the detector, an extending direction of each of the plurality of gratings being along a first direction;
a second grating group including a plurality of gratings arranged along the optical axis direction of the X-rays between the X-ray source and the detector, the second grating group being arranged side by side with the first grating group in a direction intersecting with the optical axis direction, an extending direction of each of the plurality of gratings of the second grating group being along a second direction different from the first direction;
a moving mechanism configured to relatively move a subject and an imaging system, the imaging system being composed of the X-ray source, the detector, the first grating group, and the second grating group; and
an image processing unit configured to generate a phase-contrast image based on a signal detected by the detector,
wherein the moving mechanism is configured to relatively move the subject and the imaging system such that the subject passes through a first grating region in which the first grating group is arranged and a second grating region in which the second grating group is arranged, and
wherein the image processing unit is configured to generate a first phase-contrast image when the subject has passed through the first grating region and a second phase-contrast image when the subject has passed through the second grating region.

2. The X-ray phase imaging system as recited in claim 1, wherein the first grating group and the second grating group are arranged such that the first direction and the second direction are substantially perpendicular to each other.

3. The X-ray phase imaging system as recited in claim 1, wherein the image processing unit is configured to generate a first composite image in which the first phase-contrast image and the second phase-contrast image are composed.

4. The X-ray phase imaging system as recited in claim 1, wherein the X-rays that have passed through the first grating group and the X-rays that have passed through the second grating group are each detected by a common detector.

5. The X-ray phase imaging system as recited in claim 1, wherein the first grating group and the second grating group are each arranged within an irradiation range of the X-rays emitted from a common X-ray source.

6. The X-ray phase imaging system as recited in claim 1, wherein the first grating group and the second grating group each include a first grating for enhancing coherence of the X-rays emitted from the X-ray source, a second grating for forming a self-image, and a third grating for interfering with the self-image of the second grating,
wherein the first grating of the first grating group and the first grating of the second grating group are formed integrally, the second grating of the first grating group and the second grating of the second grating group are formed separately, and the third grating of the first grating group and the third grating of the second grating group are formed separately.

7. The X-ray phase imaging system as recited in claim 1, wherein the image processing unit is configured such that based on a plurality of images captured while relatively moving the subject and the imaging system in each of the first grating region and the second grating region and phase information of Moire fringes generated in the plurality of images,
a pixel value in each pixel of the subject in the plurality of images and a phase value of the Moire fringe generated in each pixel are associated, and
based on position information of a pixel of the subject at the same position in the plurality of images and a pixel value of each pixel associated with the phase value, the first phase-contrast image and the second phase-contrast image are generated by aligning pixels of the subject at the same position in the plurality of images in each of the first grating region and the second grating region.

8. The X-ray phase imaging system as recited in claim 7, wherein the moving mechanism is configured to continuously move the subject when imaging the subject, and
wherein the image processing unit is configured to generate the first phase-contrast image and the second phase-contrast image based on the acquired continuous images.

9. The X-ray phase imaging system as recited in claim 7, wherein the moving mechanism is configured to move the subject by a predetermined distance at a time when imaging the subject, and
wherein the image processing unit is configured to generate the first phase-contrast image and the second phase-contrast image based on the image acquired while moving the subject by the predetermined distance at a time.

10. The X-ray phase imaging system as recited in claim 7, wherein the image processing unit is configured to generate position calibration data used for aligning respective pixels of the subject at the same position in the plurality of images based on a plurality of position calibration images captured while relatively moving the marker and the imaging system.

11. The X-ray phase imaging system as recited in claim 10, wherein the position calibration data is generated based on a command value related to a movement amount input to the moving mechanism when relatively moving the marker and the imaging system by the moving mechanism and a movement amount of the marker or the imaging system in the position calibration image when the marker and the imaging system are relatively moved based on the command value.

12. The X-ray phase imaging system as recited in claim 11, wherein the position calibration data is generated by acquiring an approximate expression showing a relation between the command value and the movement amount of the marker or the imaging system, based on a position of each pixel of the marker at the same position in the plurality of position calibration images.

13. The X-ray phase imaging system as recited in claim 1, wherein the image processing unit is configured to generate a phase image, based on a phase differential image when the subject has passed through the first grating region and a phase differential image when the subject has passed through the second grating region.

14. The X-ray phase imaging system as recited in claim 1, further comprising:
a position information acquisition unit configured to acquire a tomographic position of a tomographic plane which is an imaging target, in the optical axis direction,
wherein the image processing unit is configured to generate the first phase-contrast image and the second phase-contrast image in the tomographic plane, by acquiring a phase distribution in the tomographic plane, based a plurality of images in which the subject was imaged at a plurality of relative positions of the imaging system and the subject in a predetermined direction and the acquired tomographic position.

15. The X-ray phase imaging system as recited in claim 1, wherein the moving mechanism is configured to relatively move the subject and the imaging system such that the subject passes through no grating region where the first grating group and the second grating group are not arranged, and
wherein the image processing unit is configured to display the first phase-contrast image and the second phase-contrast image, and an absorption image acquired when the subject has passed through the no grating region by arranging them side by side, or display a second composite image in which the first phase-contrast image and the second phase-contrast image, and the absorption image are composed.

* * * * *